US011478008B2

(12) United States Patent
Torres Olivares et al.

(10) Patent No.: US 11,478,008 B2
(45) Date of Patent: Oct. 25, 2022

(54) FORMULATIONS COMPRISING RATFISH LIVER OIL OR A PRODUCT OF AN ENZYMATIC OR CHEMICAL GLYCEROLYSIS PROCESSING OF RATFISH LIVER OIL AND SUPERCRITICAL ROSEMARY EXTRACT AND USES THEREOF

(71) Applicants: UNIVERSIDAD AUTÓNOMA DE MADRID, Madrid (ES); IMDEA ALIMENTACION, Madrid (ES); HOSPITAL UNIVERSITARIO INFANTA SOFIA, San Sebastián de los Reyes—Madrid (ES)

(72) Inventors: Carlos Torres Olivares, Madrid (ES); Luis Vázquez De Frutos, Madrid (ES); Marta Corzo, Madrid (ES); Pablo Arranz, Madrid (ES); Ana Ramírez De Molina, Madrid (ES); Guillermo Reglero Rada, Madrid (ES); Viviana Loria Kohen, Madrid (ES); Marta Gómez De Cedrón, Madrid (ES); Juan Moreno Rubio, Madrid (ES); José Moisés Laparra Llopis, Madrid (ES); Enrique Casado Sáenz, Madrid (ES)

(73) Assignees: UNIVERSIDAD AUTÓNOMA DE MADRID, Madrid (ES); IMDEA ALIMENTACIÓN, Madrid (ES); HOSPITAL UNIVERSITARIO INFANTA SOFIA, San Sebastián de (ES)

( * ) Notice: Subject to any disclaimer, the term of this patent is extended or adjusted under 35 U.S.C. 154(b) by 0 days.

(21) Appl. No.: 16/065,639

(22) PCT Filed: Apr. 28, 2017

(86) PCT No.: PCT/ES2017/070263
§ 371 (c)(1),
(2) Date: Jun. 22, 2018

(87) PCT Pub. No.: WO2017/187000
PCT Pub. Date: Nov. 2, 2017

(65) Prior Publication Data
US 2019/0037900 A1    Feb. 7, 2019

(30) Foreign Application Priority Data

Apr. 29, 2016 (ES) ............... ES201630560

(51) Int. Cl.
| | |
|---|---|
| *A61K 36/53* | (2006.01) |
| *A23L 33/105* | (2016.01) |
| *A61K 47/44* | (2017.01) |
| *A61K 47/14* | (2017.01) |
| *A61K 9/00* | (2006.01) |
| *A61K 47/10* | (2017.01) |
| *A61K 9/08* | (2006.01) |
| *A61K 47/46* | (2006.01) |
| *A23L 33/115* | (2016.01) |
| *A61P 13/12* | (2006.01) |
| *A61P 35/00* | (2006.01) |
| *A61K 35/60* | (2006.01) |

(52) U.S. Cl.
CPC .......... *A23L 33/105* (2016.08); *A23L 33/115* (2016.08); *A61K 9/0014* (2013.01); *A61K 9/0053* (2013.01); *A61K 9/08* (2013.01); *A61K 35/60* (2013.01); *A61K 36/53* (2013.01); *A61K 47/10* (2013.01); *A61K 47/14* (2013.01); *A61K 47/44* (2013.01); *A61K 47/46* (2013.01); *A61P 13/12* (2018.01); *A61P 35/00* (2018.01)

(58) Field of Classification Search
None
See application file for complete search history.

(56) References Cited

U.S. PATENT DOCUMENTS

| 2011/0178164 A1 | 7/2011 | Cunha Dias Real Oliveira et al. |
| 2012/0082720 A1* | 4/2012 | Ang ........................ A61P 31/22 424/463 |

FOREIGN PATENT DOCUMENTS

| CN | 1327038 A | 12/2001 |
| CN | 105030678 A | 11/2015 |
| DE | 31 31 524 A1 | 2/1983 |

(Continued)

OTHER PUBLICATIONS

Mangold H. et al. Biologically Active Lipids. FEBS Letters 220(1)220—Aug. 2, 1987. (Year: 1987).*

(Continued)

*Primary Examiner* — Ralph J Gitomer
(74) *Attorney, Agent, or Firm* — Seed Intellectual Property Law Group LLP

(57) ABSTRACT

The present disclosure provides compositions comprising a supercritical rosemary extract and a lipid system comprising raffish liver oil or the product of an enzymatic or chemical glycerolysis processing of ratfish liver oil. The present disclosure also provides use of said compositions for immunotherapy potentiators or adjuvants for patients with cancer or immunological disorders; treatment of autoimmune-based immunological disorder selected from the group consisting of: rheumatoid arthritis, type I diabetes, psoriasis, celiac disease and multiple sclerosis; treatment of tumor growth, chronic lymphocytic choriomeningitis virus infection, hepatitis (B and C) virus infection, or human immunodeficiency virus infection; or prevention of kidney damage.

8 Claims, 7 Drawing Sheets

(56) References Cited

FOREIGN PATENT DOCUMENTS

| ES | 2 408 730 A1 | | 6/2013 |
|---|---|---|---|
| GB | 1194238 | * | 6/1970 |
| RU | 2 388 484 C2 | | 5/2010 |
| WO | 2010/136449 A1 | | 12/2010 |
| WO | 2010/138902 A1 | | 12/2010 |
| WO | 2012/161294 A1 | | 11/2012 |

OTHER PUBLICATIONS

Vicente G. et al. Supercritical Rosemary Extracts, Their Antioxidant Activity and Effect on Hepatic Tumor Progression. The J of Supercritical Fluids 79:101-108, Jul. 2013. (Year: 2013).*

Corzo-Martinez M. et al. Production of a Bioactive Lipid Based Delivery System from Rat Fish Liver Oil. Food and Bioproducts Processing 100(Part A)311-322, Aug. 2016. (Year: 2016).*

Gonzalez-Vallinas M. et al. Antitumor Effect of 5-Fluorouracil is Enhanced by Rosemary Extract in Both Drug Sensitive and Resistant Colon Cancer Cells. Pharmacological Research 72:61-68, Jun. 2013. (Year: 2013).*

Schmid H. et al. Alkoxy Lipids III. Metabolism 144(2)344-354, Oct. 1967. (Year: 1967).*

Al Sheyab et al., "The Effect of Rosemary (*Rosmarinus officinalis.* L) Plant Extracts on the Immune Response and Lipid Profile in Mice," *Journal of Biology and Life Science* 3(1):37-58, 2012.

Falch et al., "Natural antioxidants in cod liver oil: Pitfalls during oxidative stability assessment," in Luten et al. (eds.), *Seafood Research from Fish to Dish: Quality, Safety and Processing of Wild and Farmed Fish*, Wageningen Academic Publishers, Wageningen, Netherlands, 2006, pp. 127-136. (Abstract Only).

Iannitti et al., "An Update on the Therapeutic Role of Alkylglycerols," *Mar. Drugs* 8:2267-2300, 2010.

International Search Report, dated Jul. 20, 2017, for International Application No. PCT/ES2017/070263, 4 pages.

Yamamoto et al., "Activation of Mouse Macrophages by Alkylglycerols, Inflammation Products of Cancerous Tissues," *Cancer Research* 48:6044-6049, 1988.

Damstrup et al., "Evaluation of Binary Solvent Mixtures for Efficient Monoacylglycerol Production by Continuous Enzymatic Glycerolysis," *J. Agric. Food Chem.* 54(19):7113-7119, 2006.

Damstrup et al., "Process Development of Continuous Glycerolysis in an Immobilized Enzyme-Packed Reactor for Industrial Monoacylglycerol Production," *J. Agric. Food Chem.* 55(19):7786-7792, 2007.

Damstrup et al., "Solvent Optimization for Efficient Enzymatic Monoacylglycerol Production Based on a Glycerolysis Reaction," *JAOCS* 82(8):559-564, 2005.

Palmieri et al., "Jurassic surgery and immunity enhancement by alkyglycerols of shark liver oil," *Lipids in Health and Disease* 13:178, 2014. (5 pages).

Soler-Rivas et al., "Testing and Enhancing the in Vitro Bioaccessibility and Bioavailability of *Rosmarinus officinalis* Extracts with a High Level of Antioxidant Abietanes," *J. Agric. Food Chem.* 58(2):1144-1152, 2010.

Torres et al., "Study of the analysis of alkoxyglycerols and other non-polar lipids by liquid chromatography coupled with evaporative light scattering detector," *J. Chromatogr. A* 1078:28-34, 2005.

Torres et al., "Lipase-catalyzed glycerolysis of an oil rich in eicosapentaenoic acid residues," *Biotechnology Letters* 24:667-673, 2002.

Navarro-García et al., "Natural antioxidants in the stability of ray liver oil," *Ciência Rural* 47(1):e20160240, 2017. (7 pages).

* cited by examiner

Figure 7

| Pathway | Gene | Gene name |
|---|---|---|
| Inflammation and inflammatory response Immunomodulation | IL1B | Interleukin 1, Beta |
| | TNF (TNFA) | Tumor Necrosis Factor |
| | MAPK1 | Mitogen-Activated Protein Kinase 1 |
| | PTK2B | Protein Tyrosine Kinase 2 Beta |
| | STAT3 | Signal Transducer Activator Of Transcription 3 |
| | JAK1 | Janus Kinase 1 |
| | JAK3 | Janus Kinase 3 |
| | NFKB | Nuclear Factor Of Kappa Light Polypeptide Gene Enhancer In B-Cells 1 |
| | NLRP3 | NLR Family, Pyrin Domain Containing 3 |
| | CCL2 (MCP-1) | Chemokine (C-C Motif) Ligand 2 |
| | CXCR1 | Chemokine (C-X-C Motif) Receptor 1 |
| | CSF2 | Colony Stimulating Factor 2 (Granulocyte-Macrophage) |
| | CCL5(RANTES) | Chemokine (C-C Motif) Ligand 5 |
| | CCR5 | Chemokine (C-C Motif) Receptor 5 (Gene/Pseudogene) |
| | PLCG1 | Phospholipase C, Gamma 1 |
| | PRKCD | Protein Kinase C, Delta |
| | ADIPOQ | Adiponectin, C1Q And Collagen Domain Containing |
| | BMP2 | Bone Morphogenetic Protein 2 |
| | LIF | Leukemia Inhibitory Factor |
| | TGFB2 | Transforming Growth Factor, Beta 2 |
| | IFNG | Interferon, Gamma |
| | IL2 | Interleukin 2 |
| | IL6 | Interleukin 6 |
| | TLR4 | Toll-Like Receptor 4 |
| Oxidative stress and antioxidant response | NOS2 | Nitric Oxide Synthase 2, Inducible |
| | NOX5 | NADPH Oxidase, EF-Hand Calcium Binding Domain 5 |
| | NCF2 | Neutrophil Cytosolic Factor 2 |
| | SOD1 | Superoxide Dismutase 1, Soluble |
| | GPX1 | Glutathione Peroxidase 1 |
| | PRDX5 | Peroxiredoxin 5 |
| | NFE2L2 | Nuclear Factor, Erythroid 2-Like 2 |
| Rosemary molecular targets in colorectal cancer | DTYMK | Deoxythymidylate Kinase (Thymidylate Kinase) |
| | TK1 | Thymidine Kinase 1, Soluble |
| | GCNT3 | Glucosaminyl (N-Acetyl) Transferase 3, Mucin Type |
| | PLA2G7 | Phospholipase A2, Group VII(Platelet-Activating Factor Acetylhydrolase, Plasma) |
| Fatty acid metabolism, adipogenesis and obesity | PPARA | Peroxisome Proliferator-Activated Receptor Alpha |
| | PPARG | Peroxisome Proliferator-Activated Receptor Gamma |
| | CEBPA | CCAAT/Enhancer Binding Protein (C/EBP), Alpha |
| | CEBPB | CAAT/Enhancer Binding Protein (C/EBP), Beta |
| | SREBF1 | Sterol Regulatory Element Binding Transcription Factor 1 |
| | FASN | Fatty Acid Synthase |
| | IRS2 | Insulin Receptor Substrate 2 |
| | ACSL4 | Acyl-CoA Synthetase Long-Chain Family Member 4 |
| | GPD2 | Glycerol-3-Phosphate Dehydrogenase 2 (Mitochondrial) |
| | CHKA | Choline Kinase Alpha |
| | LEP | Leptin |
| | LEPR | Leptin Receptor |

Genes affected during nutritional intervention

| Gene | Group A* | Group B* | p |
|---|---|---|---|
| JAK1 | 0.37 (0.33) | -0.09 (0.32) | 0.02 |
| NFE2L2 | -0.13 (0.65) | -0.67 (0.76) | 0.031 |
| BMP2 | 0.79 (1.3) | -0.41 (0.7) | 0.008 |
| CHKA | -0.24 (0.7) | -0.76 (0.74) | 0.083 |
| *data expressed in -ddCt (logRQ) | | | |

FORMULATIONS COMPRISING RATFISH LIVER OIL OR A PRODUCT OF AN ENZYMATIC OR CHEMICAL GLYCEROLYSIS PROCESSING OF RATFISH LIVER OIL AND SUPERCRITICAL ROSEMARY EXTRACT AND USES THEREOF

FIELD OF THE ART

The present invention relates to the fields of food, nutrition and health. More specifically, the present invention relates to the sub-field of food for specified health use such as functional foods and nutritional supplements.

STATE OF THE ART

In the last decade, many public and private resources in Spain and Europe have been funneled into the development of functional foods with anticancer potential, among others, from natural sources. However, the expected effectiveness was not achieved in most cases, where the clinical use thereof is very limited. The new bioactive ingredients incorporated in functional foods often showed promising effects in in vitro assays but fail to offer the same efficacy in vivo in clinical studies. This is usually due to the low solubility of these compounds in water, which limits the luminal solubilization and dissolution of said compounds following their intake and leads to a low stability during gastric digestion, where their precipitation and degradation may be enhanced. All the above causes these new bioactive ingredients to have low bioaccessibility (amount of product in the intestinal tract that is soluble and therefore available for absorption) at the gastrointestinal (GTI) level and low bioavailability (capacity of the product to be absorbed by intestinal cells and to move into the bloodstream to be used by cells and organs).

This clearly shows the importance of delving deeper into the development of new formulation strategies that aim to improve these two aspects in order to obtain bioactive formulations that are effective in vivo.

BRIEF DESCRIPTION OF THE INVENTION

The inventors of the present invention solve the aforementioned technical problem by providing a lipid system which not only improves stability during digestion and oral bioavailability of various bioactive compounds in a safe and effective manner, but also in many cases enhances the effects of said compounds.

Specifically, the lipid system of the present invention is a self-emulsifiable system that forms microemulsions during digestion together with bile salts and phospholipids, forming mixed micelles which stabilize the bioactive components during digestion, preventing their precipitation or interaction with absorption inhibitors, and thereby increasing their bioaccessibility, bioavailability, and accordingly their bioactivity.

Furthermore, this system allows the lipophilization of barely water-soluble molecules, making it easier to apply them as ingredients in different foods.

Furthermore, the lipid system of the present invention comprises a proportion of glycerol ethers suitable for giving rise to free or non-esterified alkylglycerols (AKGs) capable of increasing the bioactivity of the delivered compound, even in a synergistic manner, but without significantly affecting the digestibility thereof. In this sense, the inventors have demonstrated the in vitro antiproliferative activity of said lipid system on human colon cancer cells due to its high bioactive alkylglycerol (AKG) content, a synergistic effect being observed between the antiproliferative activity of the bioactive lipid vehicle and the antiproliferative activity of the delivered compound.

Additionally, the authors of the present invention provide formulations or compositions comprising lipid systems carrying bioactive compounds for use as immunotherapy potentiators or adjuvants for patients with cancer or immunological disorders.

BRIEF DESCRIPTION OF THE DRAWINGS

FIG. 7 shows a panel of genes analyzed in relation to inflammation, immunomodulation, oxidative stress, metabolism of rosemary molecular targets and lipids in colorectal cancer.

DETAILED DESCRIPTION OF THE INVENTION

Definitions

Figure 1:
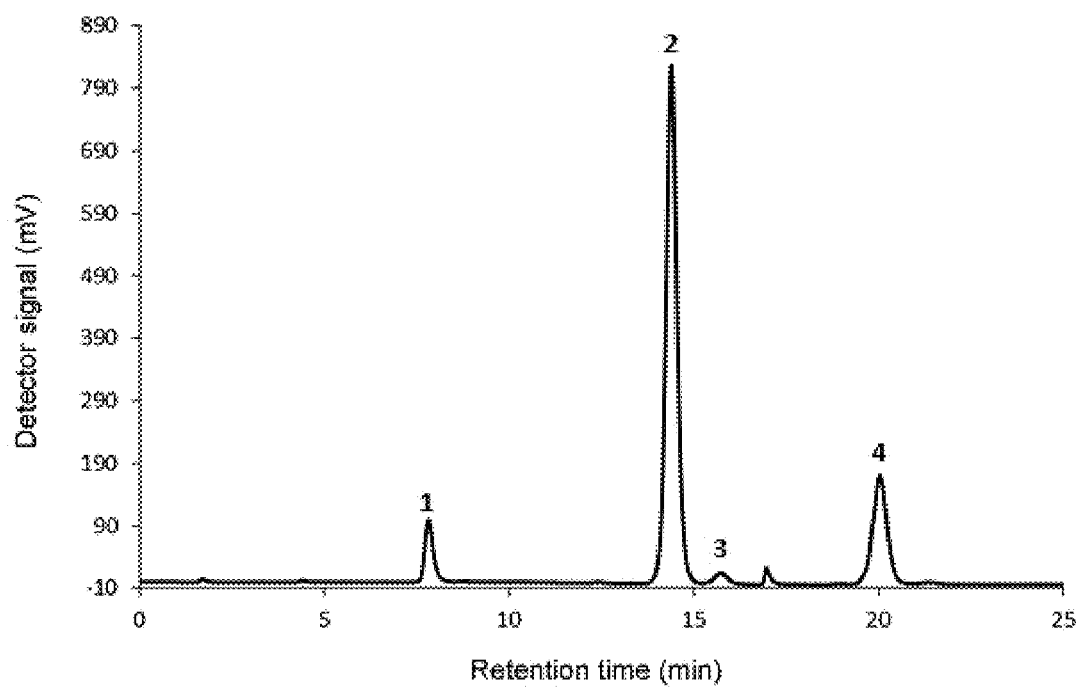
FIG. 1 shows the chromatographic profile, obtained using LC-ELSD, of the glyceride and alkylglycerol mixture obtained by means of a glycerolysis process under reaction conditions giving rise to a MAG content greater than 25% (w/w). 1=DAGE; 2=2-MAGE+1,3-DAG; 3=1,2-DAG; 4=MAG

In the present invention, "bioaccessibility" is understood as the amount of product in the intestinal tract that is soluble and therefore available for absorption.

In the present invention, "bioavailability" is understood as the capacity of the product to be absorbed by intestinal cells and to move into the bloodstream to be used by cells and organs.

In the present invention, the term "delivered SRE" refers to the supercritical rosemary extract that is combined with or incorporated in any of the lipid systems of the invention.

In the present invention, the term "formula or formulation" refers to the combination of a lipid system of the invention with a bioactive compound, either a food ingredient or a drug.

In the present invention, the term "digested non-delivered SRE" refers to the supercritical rosemary extract that is not combined with or incorporated in any of the lipid systems of the invention, and is subjected to in vitro gastrointestinal digestion before its bioaccessibility and antiproliferative activity study.

In the present invention, the term "non-digested and non-delivered SRE" refers to the supercritical rosemary extract that is not combined with or incorporated in any of the lipid systems of the invention, and is not subjected to in vitro gastrointestinal digestion before studying its antiproliferative activity.

In the present invention, the term "triglyceride (TAG)" refers to a molecule of general formula $CH_2OR_1$—$CHOR_2$—$CH_2OR_3$, where $R_1$, $R_2$ and $R_3$ represent, independently from one another, a saturated or unsaturated, linear or branched, conjugated or non-conjugated $C_1$-$C_{24}$ acyl group with or without double bonds.

In the present invention, the term "diacylglycerol (DAG)" refers to a molecule of general formula $CH_2OR_1$—$CHOR_2$—$CH_2OR_3$, where $R_1$, $R_2$ and $R_3$ represent, independently from one another, a hydrogen or a saturated or unsaturated, linear or branched, conjugated or non-conjugated $C_1$-$C_{24}$ acyl group with or without double bonds, where at least one of $R_1$, $R_2$ or $R_3$ represents a hydrogen.

In the present invention, the term "monoacylglycerol (MAG)" refers to a molecule of general formula $CH_2OR_1$—$CHOR_2$—$CH_2OR_3$, where one of $R_1$, $R_2$ or $R_3$ represents a saturated or unsaturated, linear or branched, conjugated or non-conjugated $C_1$-$C_{24}$ acyl group with or without double bonds, and the other two of $R_1$, $R_2$ or $R_3$ a hydrogen.

In the present invention, the term "diacylglycerol ether (DAGE)" refers to a molecule of general formula $CH_2OR_1$—$CHOR_2$—$CH_2OR_3$, where $R_1$, $R_2$ and $R_3$ represent, independently from one another, a saturated or unsaturated, linear or branched, $C_1$-$C_{24}$ alkyl group with or without double bonds; or a saturated or unsaturated, linear or branched, conjugated or non-conjugated $C_1$-$C_{24}$ acyl group with or without double bonds, where at least one of $R_1$ or $R_3$ represents an alkyl group.

In the present invention, the term "monoacylglycerol ether (MAGE)" refers to a molecule of general formula $CH_2OR_1$—$CHOR_2$—$CH_2OR_3$, where $R_1$, $R_2$ and $R_3$ represent, independently from one another, a hydrogen; a saturated or unsaturated, linear or branched $C_1$-$C_{24}$ alkyl group with or without double bonds; or a saturated or unsaturated, linear or branched, conjugated or non-conjugated $C_1$-$C_{24}$ acyl group with or without double bonds, where at least one of $R_1$ or $R_3$ represents an alkyl group and another one of $R_1$, $R_2$ or $R_3$ is a hydrogen.

In the present invention, the term "free or non-esterified alkylglycerol (AKG)" refers to a molecule of general formula $CH_2OR_1$—$CHOR_2$—$CH_2OR_3$, where one of $R_1$ or $R_3$ represents a saturated or unsaturated, linear or branched, conjugated or non-conjugated $C_1$-$C_{24}$ alkyl group with or without double bonds, and the other two of $R_1$, $R_2$ or $R_3$ a hydrogen.

In the present invention, the term "glycerin" refers to a molecule of general formula $CH_2OR_1$—$CHOR_2$—$CH_2OR_3$, where $R_1$, $R_2$ and $R_3$ represent, independently from one another, a hydrogen.

DESCRIPTION

The bioactivity of an orally administered substance is determined by its bioaccessibility at the gastrointestinal level following its intake (measured as the amount of product in the intestine that is soluble and available for absorption), and by its bioavailability (capacity to be absorbed by intestinal cells). This aspect is important seeing that specific compounds which have shown promising effects in in vitro assays fail to exhibit any bioactive effect in clinical studies, usually due to their low solubility in the aqueous medium of the stomach, which limits their bioaccessibility at the intestinal level and their bioavailability.

In this sense, one of the problems solved by the present invention is the use of a bioactive lipid system as a vehicle for food ingredients for health use in order to obtain highly bioaccessible and bioactive formulations.

This lipid system consists of the product of a pilot plant-scalable enzymatic glycerolysis or chemical glycerolysis process based on ratfish liver oil (RLO). Considering the characterization performed using LC-ELSD, this product (referred to hereinafter as glycerolysis product, GP) is made up of different proportions of monoacylglycerols (MAGs), diacylglycerols (DAGs), diacylglycerol ethers (DAGEs) and monoacylglycerol ethers (MAGEs), among others components. These compounds have a higher polarity and better emulsifying properties than the starting triglyceride (TAG) and diacylglycerol ether (DAGE), such that the composition of the final mixture will determine the capacity of the GP to act efficiently as a carrier lipid, the MAG content being particularly important. As described in detail in the examples of the present invention, the delivery capacity of the GP was compared with the delivery capacity of two other more readily obtained lipid systems consisting of original RLO and RLO with food grade monoolein (MO) as an emulsifier at a molar ratio of 1:1 (referred to hereinafter as RLO+MO). Unlike the GP, these systems are mainly made up of DAGE (80% w/w) and TAG (20% w/w), and DAGE (57% w/w), TAG (15% w/w) and MO (28% w/w), respectively.

The starting material chosen for obtaining the lipid systems of the invention was ratfish (*Hydrolagus colliei*) liver oil due to its exceptionally high alkylglycerol (AKG) content, which has various beneficial effects on human health, the strong antiproliferative activity thereof standing out.

As illustrated throughout the present invention, the lipid systems of the invention constitute a very interesting alternative to plant oils commonly used as carrier lipids. This interest is mainly due to their high bioactive AKG content, since a synergistic activity can be achieved between the carrier lipid and the delivered bioactive compound. Furthermore, they also constitute a novel alternative, since there are no prior studies on the use of self-emulsifiable, AKG-rich lipid systems of this type as bioactive carrier lipids.

Due to their lipophilic nature, the lipid systems of the invention can act as vehicles for bioactive food ingredients or drugs, particularly for those with limited water solubility. Among the food ingredients, natural extracts derived from plants of the Lamiaceae and Asteraceae families stand out due to their promising anticancer properties. In the present invention, a supercritical rosemary (*Rosmarinus officinalis* of the Lamiaceae family) extract (SRE) that has anticancer activity and has been extensively characterized in earlier studies has been combined in different proportions with the GP (formulation referred to hereinafter as GP+SRE) and the RLO+MO system (formulation referred to hereinafter as RLO+MO+SRE) by means of high-pressure homogenization (3 passes at 500 bars) for the sole purpose of illustrating the present invention, since, as indicated, the lipid systems of the invention can be used as a vehicle for different bioactive compounds and drugs.

Once the glycerolysis product (GP) indicated above has been obtained, it was duly characterized, as described in the examples, providing the following qualitative and quantitative composition:
  about 30% (w/w) of monoglycerides;
  about 1% (w/w) of triglycerides;
  about 20% of diacylglycerol ethers (DAGEs);
  about 2% of glycerin; and
  about 47% of a diacylglycerol and monoacylglycerol ether (MAGE) mixture.

Figure 4:
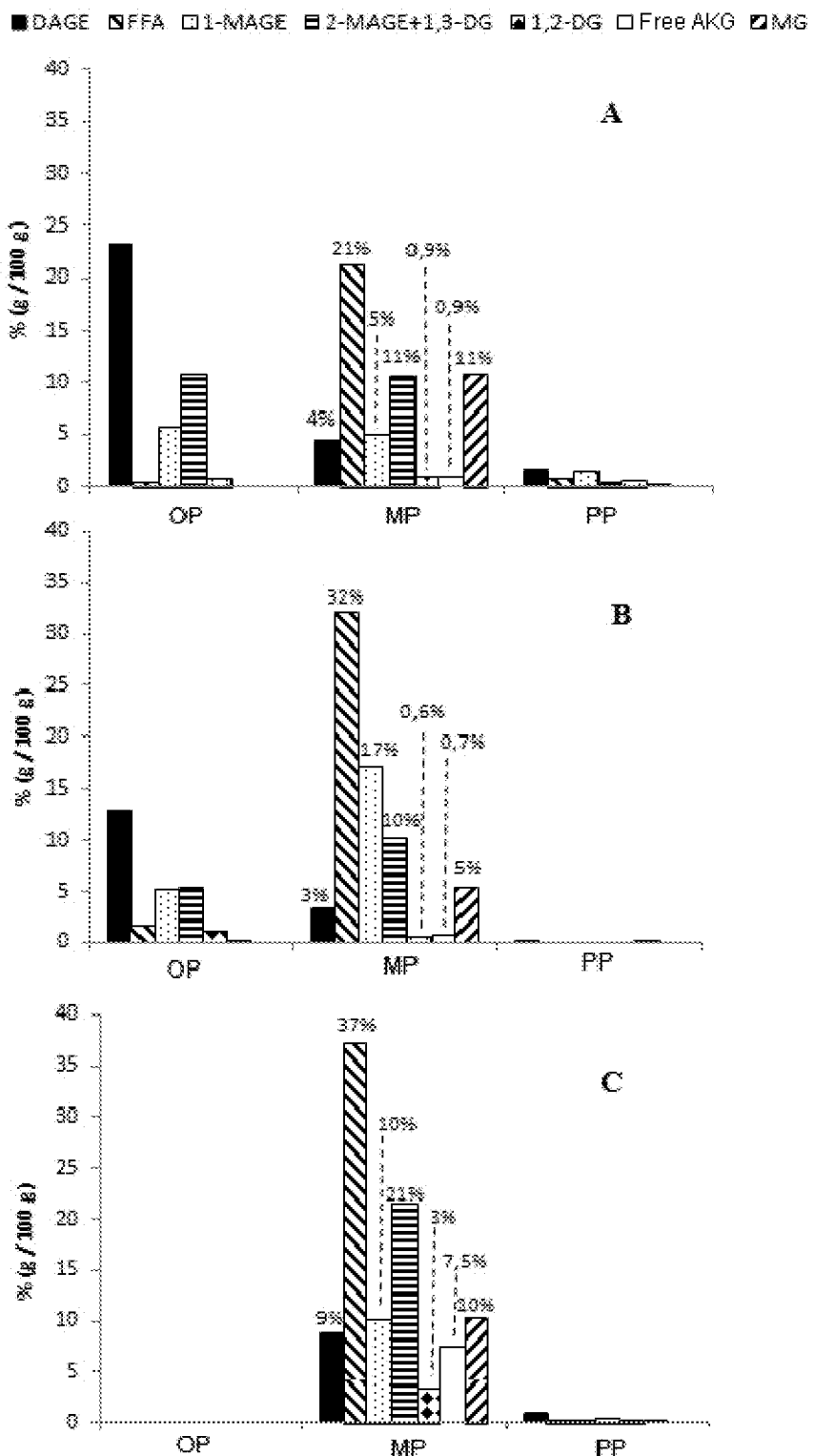
FIG. 4 shows the lipid composition of the different phases (OP, MP and PP) obtained after centrifugation of the end products of the digestion of original RLO (A), RLO+MO (B) and GP (C).

Said composition was used to carry out the experiments which are described in the examples and aim to check for suitability of this lipid system as a vehicle for bioactive substances and the impact on their bioaccessibility and bioavailability. According to the results obtained from the digestibility study, it is particularly abundant in the end product of the digestion of the GP, in which almost 98.5% (w/w) of the lipid fraction is in the form of mixed micelles or vesicles, indicating that virtually all the products released from the hydrolysis of the lipid system GP are potentially bioaccessible. In contrast, the RLO+MO (RLO+monoolein) systems, and particularly original RLO (see examples), are significantly less bioaccessible than the lipid system indicated above (hereinafter, GP), since only about 75 and 54% (w/w), respectively, of the lipid fraction is in the MP, whereas about 22 and 41% (w/w), respectively, is part of the oily phase, made up essentially of undigested DAGE and MAGE. It must be pointed out that in the digested GP, MAGE is mainly in micellar form and is therefore bioaccessible. Likewise, it is also important to highlight the high percentage of free AKG (about 7.5% w/w) in the MP of the digested GP in comparison with that in the MP of the RLO+MO system (about 1% w/w) and original RLO (about 0.7% w/w) (FIG. 4). According to various studies carried out previously with colon cancer cell cultures, both MAGE, and particularly free AKG, are potentially more bioactive than DAGE.

Based on the digestibility and bioaccessibility results, original RLO was ruled out as a potentially effective vehicle for bioactive substances, such as SRE (supercritical rosemary extract). This is why SRE formulations are only obtained in the present invention with GP (GP+SRE) and RLO+MO (RLO+MO+SRE) lipid systems. The incorporation of 4% (w/w) and 9% (w/w) of SRE does not significantly affect the bioaccessibility of the lipid fraction, observing a distribution of phases (OP, MP and PP) and a lipid composition of each of said phases similar to that of the SRE-free GP and RLO+MO systems (FIG. 4).

Based on this, the results that have been obtained indicate that the delivery of 9% of SRE with the RLO+MO system, and particularly the GP system, efficiently increases SRE stability during digestion, and accordingly its bioaccessibility at the intestinal level and its antiproliferative effect.

Furthermore, in the case of the GP+9% SRE formulation, the bioactive ingredient (AKG and SRE) content of the MP at the concentration required to reach IC50 (50.23 µM AKG$_t$ and 3.14 µg/mL SRE) is less than for the GP (124.54 µM AKG$_t$) and the non-digested and non-delivered SRE (IC50~40 µg/mL) separately, indicating a synergistic effect between the lipid vehicle and the delivered SRE.

Therefore, the lipid system of the invention has a specific qualitative and quantitative composition which is particularly useful for delivering bioactive formulations and improving the bioaccessibility and bioavailability of said formulations in vivo.

Therefore, a first aspect of the invention relates to a composition or lipid system comprising:
  a. between 25% and 35% (w/w) of emulsifying substances such as monoglycerides and/or free alkylglycerols;
  b. between 10% and 25% (w/w) of diacylglycerol ethers (DAGEs); and
  c. between 40% and 60% (w/w) of monoacylglycerol ethers (MAGEs) and/or diacylglycerols (DAG), where the proportion of MAGEs with respect to the total amount of MAGEs and DAGs present in the lipid system is at least 50% (w/w), more preferably at least 60, 70, 80, 85, 90 or 95%.

With respect to the composition described in detail above, it is important to point out that when the monoglycerides or a component with emulsifying capacity, such as free or non-esterified alkylglycerol (AKG), is below 25%, the system of the invention loses its self-emulsifying capacity which would seriously affect the bioaccessibility and digestibility of the system. Therefore, the first component (monoglycerides) may be replaced or complemented with any other emulsifier, such as monoglycerides and/or AKG, provided that the sum of the emulsifying components is kept in a proportion between 25 and 35% (w/w) of the total weight of the end product.

Furthermore, the established percentage of DAGEs in the lipid system of the invention must always be equal to or less than 25% (w/w) given that the inventors of the present invention have proven that amounts above this percentage will negatively affect product accessibility and digestibility. On the other hand, DAGEs must not be present in amounts less than 10% given that these components protect the delivered active ingredient in the first part of digestion.

Finally, the diacylglycerol and monoacylglycerol ether (MAGE) mixture of the composition must be in a proportion of 50:50 or in a proportion of >50% of MAGEs with respect to the sum of MAGEs and diglycerides. MAGEs are essential for the synthesis, accessibility and bioavailability of AKGs in a proportion sufficient for increasing (potentially in a synergistic manner) the action of the active ingredient (for example, natural extracts that are rich in: phenolic compounds, flavonoids, terpenoids, saponins, sterols, polyphenols, etc., or bioactive substances or drugs the Log P* of which is greater than 2, where Log P* is the log of the ratio between the concentrations of the non-ionized solute in octanol solvents and water and is determined according to the following formula:

$$\log P_{octanol/water} = \log\left(\frac{[\text{Solute}]_{octanol}}{[\text{Solute}]_{water}^{non\text{-}ionized}}\right)$$

On the other hand, diglycerides must preferably be present in the lipid system of the invention given that they help in the digestibility of the possible triglycerides present in the composition.

In a preferred embodiment of the first aspect of the invention, the composition or lipid system comprises:
a. between 25% and 35% (w/w) of monoglycerides and/or free alkylglycerols;
b. between 10% and 25% (w/w) of diacylglycerol ethers (DAGEs);
c. between 0 and 5% (w/w) of triglycerides;
d. between 0 and 3% of glycerin; and
e. between 40% and 60% (w/w) of monoacylglycerol ethers (MAGEs) and/or diacylglycerols (DAGs), where the proportion of MAGEs with respect to the total amount of MAGEs and DAGs present in the lipid system is at least 50% (w/w).

In another preferred embodiment of the first aspect of the invention, the composition or lipid system comprises:
a. between 28% and 32% (w/w) of monoglycerides and/or free alkylglycerols;
b. between 18% and 22% (w/w) of diacylglycerol ethers (DAGEs);
c. between 0 and 2% (w/w) of triglycerides;
d. between 1% and 3% of glycerin; and
e. between 40% and 50% (w/w) of monoacylglycerol ethers (MAGEs) and/or diacylglycerols (DAGs), where the proportion of MAGEs with respect to the total amount of MAGEs and DAGs present in the lipid system is at least 50% (w/w).

A second aspect of the invention relates to a process for obtaining a composition or lipid system comprising:
a. adding ratfish liver oil (RLO), preferably the oil with the qualitative and quantitative characteristics described in Table 1, in a vessel;
b. regulating the temperature of the product of step a) preferably to 40° C. with continuous stirring (200 rpm);
c. adding one or more lipases to the mixture of step b);
d. incubating the product of step c), preferably in an orbital stirrer at 200 rpm (IKA KS 4000 ic Control, Staufen, Germany); and
e. obtaining the glycerolysis reaction product.

The process for obtaining a composition or lipid system preferably comprises:
a. adding ratfish liver oil (RLO), preferably the oil with the qualitative and quantitative characteristics described in Table 1, in a vessel comprising glycerol, preferably at an RLO:glycerol molar ratio of 1:1, and preferably adding a solvent to the oil and glycerol mixture improving their miscibility;
b. regulating the temperature of the mixture of step a) preferably to 40° C. with continuous stirring (200 rpm);
c. adding one or more lipases to the mixture of step b);
d. incubating the product of step c), preferably in an orbital stirrer at 200 rpm (IKA KS 4000 ic Control, Staufen, Germany); and
e. obtaining the glycerolysis reaction product.

Specifically, the process for obtaining the lipid system used can be arrived at by performing glycerolysis reactions under specific stirring, temperature and time conditions (continuous stirring at 200 rpm and 40° C. for 48 hours) in the following manner starting from a vessel with glycerol: in the presence of GRAS solvents, including CPN, HXL and CPME. To calculate the required volume of solvent, 1 ml of solvent aliquots was successively added until the complete dissolution of the glycerol present in the initial reaction mixture. Next, the glycerol-solvent solutions were mixed with RLO in 250 ml flasks at the same molar ratio as in the solvent-free reactions (glycerol:RLO of 1:1). After mixing with RLO, the glycerol once again became partially insoluble, but system homogeneity remained higher than in the absence of a solvent. The reaction was started with the addition of lipase, and in this case, in order to counteract the dilution effect of the solvent, the enzymatic load (enzyme:RLO ratio=1.25:10 w/w) was greater than that used in solvent-free systems. After the reaction, the solvent was removed from the reaction product through evaporation at 50° C. and in vacuum (~0.10 kPa) using an RV 10 rotary evaporator (IKA®-Werke GmbH & Co. KG, Staufen, Germany) and vacuum from an oil-sealed rotary vacuum pump (Edwards, distributor in Spain *Iberica* Vacuum, Madrid, Spain).

A third aspect of the invention relates to a composition or lipid system that is obtained or can be obtained by means of the process of the third aspect of the invention.

At this point it must be highlighted that, besides the lipid system of the invention which has a specific qualitative and quantitative composition that is particularly useful for delivering bioactive formulations and improving the bioaccessibility and bioavailability of said formulations in vivo, the authors of the present invention have found out that other lipid compositions similar to those of the invention show a very interesting therapeutic potential. In this sense, it is important to highlight the content of Example 7, where an 8-week double-blind, parallel, randomized study was conducted in which 57 healthy volunteers (58.6% being women) with a mean age of 27.9±10.1 years old were included, 30 of whom belonged to the study group and 27 to the control group.

In this study, the participants took one capsule with lunch or dinner. The soft gelatin capsules contained RLO-derived alkylglycerols, rosemary extract and monostearin of the following characteristics:
RLO: shark liver oil with 20% alkylglycerols (Gustav Heess): 750 mg (providing 150 mg of alkylglycerols).
SRE: rosemary antioxidant extract, 25% diterpene phenols, type no. 027.020 (*Rosmarinus officinalis* L.) 45 mg (providing 11.25 mg of diterpene phenols).
MS: food-grade glycerol monostearate.
Composition: 91.2% RLO+5.2% SRE+3.6% MS.

In said study, after drawing blood PBMCs were isolated and then cultured with LPS for measuring cytokines in the supernatant, in which the levels of IL1β; IL 2, 4, 5, 6, 8, 10, IFNý, TNFα were measured using, to that end, Human High Sensitivity T Cell Magnetic Bead Panel kit and taking readings with MagPix.

The CD (cluster of differentiation) count was also performed for clusters of differentiation CD3+, CD4+; CD8+, CD14+, CD16+, CD56+ on CD45+, using to that end kits and antibodies that are specific for flow cytometry.

In addition to the anthropometric control, the control of vital signs and the recording of tolerance and adverse effects, the levels of urea, creatinine, liver enzymes GOT/GPT/GGT, bilirubin and FA were evaluated as safety and follow-up parameters in the first, interim and final visits.

The immunomodulatory influence of the treatment was evaluated by generating an array of bivariate correlations (principal component analysis) for the purpose of showing the biological correlation between plasma concentrations of cytokines produced by mononuclear cells isolated from peripheral blood, and the immunological response (Th1, effector response and Th2, tolerance response).

As shown in the results of Example 7, taking capsules containing RLO-derived alkylglycerols, rosemary extract and monostearin, led to a resulting trend in the cytokine profile and leukocyte phenotyping which in turn reflects an anti-inflammatory environment that is favorable towards innate immune system polarization to effector cells of the following type: non-classical monocytes and NK cells with phagocytic capacity and cytotoxic activity preventing tumor development. Therefore, the analysis of immunological parameters (cytokines and leukocyte phenotyping) in volunteers who took the nutritional supplement for 8 weeks indicates a positive immunonutritional influence consisting of:
- innate immune response activation and tolerance.
- intermediate polarization of the immune response towards effector cells with phagocytic activity (monocytes) and cytotoxic activity (NK cells).
- production of a cytokine profile with anti-inflammatory and antitumor activity.

These results are surprising given that other studies that have been conducted with alkylglycerols alone have only shown the stimulation and activation of the adaptive response. However, in the present study where the alkylglycerols are complemented with SRE, a clear stimulation of the innate response along with an intermediate M1/M2 polarization, a unique effect found in this complement, is observed, where this modulation of the innate response is potentially effective both in cancer and in disorders of the immune system.

These results therefore suggest the use of compositions comprising alkylglycerols (preferably derived from ratfish liver oil (RLO)) complemented with SRE as:
- Agents preventing the development of metastasis in patients with cancer with localized tumors.
- Agents enhancing immunotherapy in candidate patients, in which the activation of the innate response towards the production of mature effector cells with phagocytic capacity-monocytes, NK cells-, the production of cytokines with antitumor activity and the functional maturation of T-lymphocytes targeting tumor antigens, is required.
- Agents preventing immunological disorders.

A fourth aspect of the invention therefore relates to a composition comprising supercritical rosemary extract and a lipid system in turn comprising ratfish liver oil or the product of an enzymatic or chemical glycerolysis process based on ratfish liver oil. It must be pointed out that said composition can be characterized by being a single composition or a combined composition, where the combined composition would include composition A comprising the supercritical rosemary extract and composition B comprising ratfish liver oil or the product of an enzymatic or chemical glycerolysis process based on ratfish liver oil. Said combined composition can be administered to a patient simultaneously or sequentially; in the context of the present invention, the administration would preferably be simultaneous.

In a preferred embodiment of the fourth aspect of the invention, the composition or combined composition comprises supercritical rosemary extract, a lipid system in turn comprising ratfish liver oil and MAGs or monoglycerides, preferably between 2% and 30% w/w of MAGs or monoglycerides, preferably between 3% and 30% w/w of MAGs or monoglycerides, including the end values of these ranges, more preferably, where the monoglycerides are selected from the list consisting of monoolein (MO) and monostearin (MS). More preferably, the composition of the fourth aspect of the invention comprises 91.2% w/w of RLO, 5.2% w/w of SRE and 3.6% w/w of MS, including variations of +/−30%, preferably variations of +/−20%, more preferably variations of +/−10%, even more preferably variations of +/−5%, even more preferably variations of +/−2%, even more preferably variations of +/−1%, with respect to these percentages.

In another preferred embodiment of the fourth aspect of the invention, the composition or combined composition comprises supercritical rosemary extract and a lipid system in turn comprising the composition described in the first or third aspect of the present invention or in any of the preferred embodiments thereof.

It must be pointed out that the compositions of the fourth aspect of the invention will preferably be used as immunotherapy potentiators or adjuvants for patients with cancer or immunological disorders, which immunological disorders preferably require the activation of the innate response towards the production of mature effector cells with phagocytic capacity-monocytes, NK cells-, the production of cytokines with antitumor activity and the functional maturation of T-lymphocytes targeting tumor antigens. The reason the compositions of the fourth aspect of the invention have these therapeutic applications is based on the results described in Example 7, where the physiological importance of the response in the monocyte population with respect to treatment allows assuming a positive influence thereof as part of adjuvant, preventive and/or therapeutic therapies, in order to prolong the cellular immune response. 'Immunological exhaustion' is well-defined in situations of tumor growth, as well as chronic lymphocytic choriomeningitis virus infection, hepatitis (B and C) virus infection, human immunodeficiency virus infection. Furthermore, the preservation of antigen processing by cell populations originated from monocytes may have significant positive consequences, reducing the severity and/or risk in autoimmune-based pathologies (i.e., such as rheumatoid arthritis, type I diabetes, psoriasis, celiac disease, multiple sclerosis). An increased innate immune response is also very important in the prevention of kidney damage (caused, for example, by contrasts used in medical procedures). The compositions of the fourth aspect of the invention may therefore be used in the treatment of a patient with an autoimmune-based immunological disorder, preferably selected from the list consisting of rheumatoid arthritis, type I diabetes, psoriasis, celiac disease and multiple sclerosis. Furthermore, the compositions of the fourth aspect of the invention may be used in the treatment of a patient with tumor growth, as well as with chronic lymphocytic choriomeningitis virus infection, hepatitis (B and C) virus infection, or human immunodeficiency virus infection. Finally, the compositions of the fourth aspect of the invention may be used in the prevention of kidney damage.

With respect to the use of the compositions of the fourth aspect of the invention for treating tumor growth, the following is highlighted. Monocytes are direct precursors of macrophages derived from hematopoietic stem cells. It is important to maintain a suitable 'vigilant' population given that after being taken into the tumor tissue, they can differentiate into tumor-associated macrophages, a cell population that is highly heterogeneous in terms of phenotype and pro-tumor function, supporting tumor initiation, local progression and distant metastasis. Therefore, the activation of the innate response caused by the compositions of the fourth aspect of the invention may, a priori, be interesting for treating all types of tumors, since the immune system would be able to recognize the tumors and attack them. This would be particularly interesting in those inactivated tumors with inactive lymphocytes or without any lymphocyte in the tumor. The prototype of tumors of this type is the colorectal tumor, in which except for the hypermutated ones, the others do not work on an immunological level. Other tumors in which the compositions of the fourth aspect of the invention would be particularly effective would be tumors of the digestive system (including liver and pancreas) or breast tumors, as well as melanoma, lung tumors in smokers, bladder tumors and head and neck tumors.

A fifth aspect of the invention refers to the use of the composition according to any of the first, third or fourth aspects for the elaboration of a pharmaceutically acceptable or food-grade vehicle for functional foods, nutraceutical products, natural extracts or drugs, preferably anticancer drugs.

In a preferred embodiment of the fifth aspect of the invention, said functional foods, nutraceutical products, natural extracts or drugs are characterized by having a Log P* greater than 2, where Log P* is the log of the ratio between the concentrations of the non-ionized solute in octanol solvents and water and is determined according to the following formula:

$$\log P_{octanol/water} = \log\left(\frac{[\text{Solute}]_{octanol}}{[\text{Solute}]_{water}^{non-ionized}}\right)$$

In another preferred embodiment of the fifth aspect of the invention, the nutraceutical products are selected from the list consisting of icosapent, vitamin A, vitamin E, cholecalciferol (vitamin D), alfacalcidol, calcitriol, xanthophyll, calcidiol, ethyl icosapent, ergocalciferol, dihomo-gamma-linolenic acid, clopidogrel, alpha-linolenic acid, lipoic acid and tretinoin.

In another preferred embodiment of the fifth aspect of the invention, the drugs are selected from the list consisting of vinorelbine, bexarotene, testolactone, enzalutamide, bicalutamide, vindesine, ruxolitinib, estropipate, lapatinib, regorafenib, plicamycin, anastrozole, drostanolone, irinotecan, ixabepilone, valrubicin, erlotinib and lenvatinib.

In another preferred embodiment of the fifth aspect of the invention, the drugs are selected from the list consisting of ritonavir, masoprocol, eletriptan, temazepam, benzatropine, terconazole, diatrizoate, venlafaxine, travoprost, etomidate, etonogestrel, ropivacaine, zolmitriptan, tolcapone, indomethacin and pimecrolimus.

A sixth aspect of the invention relates to a pharmaceutical composition comprising the composition or the lipid system according to any of the first, third or fourth aspects.

A seventh aspect of the invention relates to a food composition comprising the composition or the lipid system according to any of the first, third or fourth aspects.

An eighth aspect of the invention relates to the pharmaceutical composition according to the sixth aspect of the invention, where said composition delivers a drug selected from the list identified in any of the preferred embodiments of the fifth aspect of the invention. Said composition is preferably used for the elaboration of a medicinal product for the treatment of cancer, preferably for the treatment of colon cancer.

A ninth aspect of the invention relates to the food composition according to the seventh aspect of the invention, where said composition delivers a nutraceutical product selected from the list identified in the preferred embodiment of the fifth aspect of the invention.

The following specific examples provided in this patent document serve to illustrate the nature of the present invention. These examples are included only for illustrative purposes and must not be interpreted as limitations to the invention herein claimed. The examples described below therefore illustrate the invention without limiting the field of application thereof.

EXAMPLES

Materials and Methods
    Chemical Products and Reagents
    The ratfish liver oil (RLO) was kindly provided by Rosita RatfishOil® (Helgeland, Norway).
    The food-grade monoolein (99%) and the solvents used in the glycerolysis processes, including cyclopentanone (CPN), hexanal (HXL) and cyclopentyl-methyl-ether (CPME), were food-grade flavoring agents obtained from Sigma-Aldrich (San Luis, Mo., USA). The glycerol was obtained from ICN Biomedicals (Aurora, Ohio). Biocatalysts such as Novozym 435 (Nov435) (*Candida antarctica*) were kindly supplied by Novozymes A/S (Bagsvaerd, Denmark). Lipases PLG (*Alcaligenes* sp.), SL (*Burkholderia cepacia*) and TL (*Pseudomonas stutzeri*) were acquired from Meito Sangyo CO. LTD (Tokyo, Japan) and lipase DF 15 (*Rizhopus oryzae*) was acquired from Amano Enzyme Inc. (Nagoya, Japan).
    In terms of the reagents used for chromatographic analysis, the pure oleic acid (99% purity), monoolein (99% purity) and batyl alcohol (99% purity) standards were obtained from Sigma-Aldrich (San Luis, Mo., USA), whereas the pure ethyl oleate (98% purity) standard was acquired from Acros Organics (Geel, Belgium). The isooctane was obtained from Carlo Erba Reagents (Val de Reuil, France). The hexane, methyl-tert-butyl-ether (MTBE) and chloroform were obtained from Lab-Scan (Gliwice, Poland), and the formic acid (98% purity) was obtained from Panreac (Barcelona, Spain). All these solvents were HPLC-grade solvents.
    Chromatographic Characterization of the Starting Ratfish Liver Oil
    The RLO fatty acid profile was determined by means of gas chromatography with flame ionization detector (GC-FID) after methylation of the esterified fatty acid residues present in the sample. To that end, 50 MAG of RLO were dissolved with 1 ml of n-hexane (Lab-Scan, Gliwice, Poland). Next, 1 ml of 0.5 N NaOH in methanol was added for methanolysis of the sample, followed by stirring for 1 minute, heating at 100° C. for 5 minutes and additional methylation by means of adding 1 ml of 14% $BF_3$ in methanol (Supelco, Pasadena, USA), stirring for 1 minute and incubating at 100° C. for 5 minutes. The resulting fatty acid methyl ester (FAME) mixture was extracted with n-hexane (1 ml) and a saturated NaCl solution (1 ml), after stirring for 2 minutes at room temperature. The decanted hexane phase was then left to settle for 2 hours with anhydrous sodium sulfate (Panreac) to remove moisture. Finally, the hexane was evaporated to dryness to obtain a FAME residue which was then dissolved in n-hexane at a final concentration of 15 MAG·$ml^{-1}$. The chromatographic analysis of MAGEs was performed in an Agilent Technologies gas chromatograph (6850 N Network GC System) equipped with a flame ionization detector (FID). One µl of sample was injected in the division/non-division mode (division ratio of 10:1) into an HP-88 capillary column ((88% cyanopropyl)aryl-polysiloxane, 30 m×0.25 mm×0.20 µm thick; Agilent Technologies Inc., Santa Clara, Calif., USA). Helium at a flow rate of 0.9 ml/min was used as the carrier gas. The temperatures of the injector and detector were 220 and 250° C., respectively. The temperature program was as follows: starting at 50° C. and then heating to 180° C. at 20°

C./min; followed by heating from 180 to 220° C. at 15° C./min. The final temperature (220° C.) was maintained for 10 minutes. For quantification, a calibration curve was plotted with ethyl oleate. Data was obtained and integrated using the Agilent ChemStation Reb. 4B. 03.01 software (Wilmington, Del., USA). The analysis was performed in duplicate and the data was expressed as the mean±standard deviation (SD).

The starting RLO lipid profile was also evaluated by means of evaporative light scattering detector-coupled liquid chromatography (LC-ELSD). The preparation of the samples and the chromatographic method used are described below.

Glycerolysis Reaction

Lipase-catalyzed glycerolysis was performed according to the method of Torres et al. (2002) with slight modifications. In summary, 10 g of RLO were added to a 120 ml flask containing 1 g of glycerol (RLO:glycerol molar ratio of 1:1). A stoichiometric ratio of RLO and glycerol was used to prevent the presence of excess reagent in the product mixture. The temperature of the mixture was regulated to 40° C. with continuous stirring (200 rpm). The reaction was started with the addition of different commercial lipases at an enzyme:RLO ratio of 1:10 (w/w). Next, the flasks were covered and incubated in an orbital stirrer at 200 rpm (IKA KS 4000 is Control, Staufen, Germany). Progression of the glycerolysis reaction was determined by taking aliquots (50 µl) of the reaction mixture periodically. All the assays were left to settle for 48 hours and were performed in duplicate.

Glycerolysis Process Optimization

To elaborate the lipid system of the present invention (the system described in Example 2), additional glycerolysis reactions were performed under the same stirring, temperature and time conditions (continuous stirring at 200 rpm and 40° C. for 48 hours) in the following manner:

i) In the presence of GRAS solvents, including CPN, HXL and CPME. To calculate the required volume of solvent, 1 ml of solvent aliquots was successively added until the complete dissolution of the glycerol present in the initial reaction mixture. Next, the glycerol-solvent solutions were mixed with RLO in 250 ml flasks at the same molar ratio as in the solvent-free reactions (glycerol:RLO of 1:1). After mixing with RLO, the glycerol once again became partially insoluble, according to different authors (Damstrup et al., 2005, 2006, 2007), but system homogeneity remained higher than in the absence of solvent. The reaction was started with the addition of lipase, and in this case, in order to counteract the dilution effect of the solvent, the enzymatic load (enzyme:RLO ratio=1.25: 10 w/w) was greater than that used in solvent-free systems. After the reaction, the solvent was removed from the reaction product through evaporation at 50° C. and in vacuum (~0.10 kPa) using an RV 10 rotary evaporator (IKA®-Werke GmbH & Co. KG, Staufen, Germany) and vacuum from an oil-sealed rotary vacuum pump (Edwards, Distributor in Spain *Iberica Vacuum*, Madrid, Spain).

Analysis of Glycerolysis Mixtures by Means of Liquid Chromatography

The chromatographic separation and quantification of the lipids present in the original RLO sample and in the samples resulting from the glycerolysis process were performed by means of LC-ELSD. 50 µl aliquots removed from the reaction mixture throughout the entire glycerolysis process were dissolved in 2 ml of chloroform and filtered (0.45 µm PVDF filters, Symta, Madrid, Spain). The chloroform was then evaporated at 40° C. in a nitrogen stream using a Stuart SBH200D/3 block heater (Staffordshire, United Kingdom) until a residue having a constant weight was obtained. Finally, the original RLO sample or the samples resulting from the enzymatic glycerolysis were diluted with chloroform at a final concentration of 20 MAG ml$^{-1}$ before injection (1 µl, ~20 µg of total lipids) into the HPLC system.

In the presence of GRAS solvents, 200 µl aliquots were centrifuged at 10000 rpm for 3 minutes to remove possible enzyme residues. Next, 50 µl of supernatant were weighed and diluted 20 times with chloroform before injection (1 µl, ~20 µg of total lipids) into the HPLC system.

The LC-ELSD analyses were performed using an Agilent Technologies Series 1200 HPLC system (Santa Clara, Calif., USA) containing a thermostatted column compartment, a quaternary pump, an autosampler, a vacuum degasser and an evaporative light scattering detector (ELSD) (Agilent 1260 Infinity). The ELSD conditions were $2\times10^5$ Pa, 50° C., and a gain of 4 which was adjusted to precisely quantify minor compounds. Chromatographic separations were performed in an Agilent Poroshell column (Sil 2.7 µm, 4.6×100 mm) at 35° C., with a flow rate of 2 ml/min and eluents of mixture A (100% isooctane), B (0.02% (v/v) formic acid in isooctane:MTBE (50:50 v/v)) and C (MTBE:propan-2-ol (50:50 v/v)) to form a ternary gradient system as described previously by Torres et al. (2005). This methodology allows the simultaneous analysis of up to 18 classes of different neutral lipids, particularly diacylglycerol ether (DAGE), triacylglycerol (TAG) and their hydrolysis products (monoacylglycerol ether (MAGE), non-esterified alkylglycerol (Guney, 2002), monoacylglycerol (MAG) and diacylglycerol (DAG)), including different regioisomers, with a very similar structure and polarity. The injection volume was 1 µl (~20 µg of total lipids). The data was obtained and processed by means of the Agilent Chem Station software (Agilent Technologies, Boblingen, Germany).

Lipids in the reaction mixtures were identified by means of comparing their retention times ($t_R$) with the retention times of different standard lipids. Commercial oleic acid and batyl alcohol were used to identify free fatty acids (FFAs) and AKG, respectively. DAGE and TAG were identified by means of using commercial RLO and menhaden oil (Mbanya et al., 2003). Finally, the products derived from menhaden oil glycerolysis and purified by means of semipreparative HPLC were used to identify MAGE, DAG and MAG. The quantitative analysis was performed by means of the external standard method, using the calibration curves of each standard in the range of 0.4-25 MAG·ml$^{-1}$. The relative standard deviation values were below 10% in all cases.

The quantitative data was expressed as DAGE and TAG conversion during the glycerolysis process (E1) and as the percentage of each compound of the reaction mixture by weight with respect to the total weight of the reaction mixture (E2).

$$100-[(\%_{final}/\%_{initial})\times 100] \quad [E1]$$

$$[P_{comp}/P_{r.m}]\times 100 \quad [E2]$$

Where $\%_{final}$ and $\%_{initial}$ are, respectively, the final and initial percentages of DAGE and TAG in the reaction mixtures and $P_{comp}$ and $P_{r.m}$ are the weight of each compound of the reaction mixture and the total weight of the reaction mixture, respectively.

Finally, the parameters defined below were used to evaluate glycerolysis efficiency in terms of MAG production:

i) The yield (g of MAG/100 g of RLO) represents the mass of MAG obtained during glycerolysis per unit of initial mass of RLO.

ii) The productivity (g $L^{-1}h^{-1}$) represents the concentration of MAG produced per unit of reaction time.

These parameters were evaluated at the time point in which the maximum concentration of MAG in the different tested glycerolysis conditions is achieved.

Scaling to Pilot Plant

The glycerolysis reaction under specific optimum conditions was scaled to a pilot plant in a "kiloclave" reactor system (Buchi Glas Uster, Büchiglasuter, Switzerland) with mechanical stirring and controlled temperature throughout the entire process. The composition of the initial reaction mixture was adjusted to a final weight of about 500 g, consisting of 128 g of RLO, 12.8 g of glycerin and 304 g of PCN. During the reaction, lipase (12 g) was placed in a basket which was coupled to the stirring shaft of the reactor with the reaction mixture circulating through said basket. The amount of lipase used as a biocatalyst was limited by the capacity of the basket, such that the enzymatic load (enzyme:RLO ratio=0.94:10 w/w) was less than at laboratory scale. Similar to the laboratory scale, aliquots were periodically removed from the reaction mixture to study the reaction kinetics. They were analyzed by means of LC-ELSD, as explained in section 2.5. After 48 hours of reaction, the reaction medium was cleared out through the discharge valve of the reactor.

Ratfish Liver Oil Characterization

Table 1 shows the fatty acid profile of ratfish liver oil (RLO) determined by means of CG-DIL. As observed, the main fatty acids of RLO are oleic and palmitic acids and the polyunsaturated fatty acid (PUFA) content is lower in comparison with the PUFA content of other fish oils. This fatty acid profile may provide greater stability against oxidation in comparison with other marine oils.

Similarly, according to the LC-ELSD analysis, the original RLO was mainly made up of two compounds, i.e., diacylglycerol ether (DAGE, peak 1, $t_R$=6.7 minutes) and triacylglycerol (TAG, peak 2, $t_R$=7.7 minutes). The DAGE content (80% w/w) of RLO was much higher than the TAG content (20% w/w) which, as discussed above, makes it interesting to use this oil as a starting material in glycerolysis processes for designing bioactive lipid release systems, and sets said processes apart from those previously performed based on plant oils or even shark liver oil, which also contains alkylglycerols but at a substantially lower level.

TABLE 1

Ratfish liver oil fatty acid composition

| Fatty acid methyl esters | Concentration (% w/w) |
|---|---|
| Myristic acid (C14:0) | 1.0 |
| Palmitic acid (C16:0) | 12.8 |
| Palmitoleic acid (C16:1) | 6.0 |
| Hexadecadienoic acid (C16:2) | 1.5 |
| Hexadecatrienoic acid (C16:3) | 1.9 |
| Stearic acid (C18:0) | 5.5 |
| Oleic acid (C18:1) | 43.3 |
| γ-linolenic acid (C18:3) | 4.0 |
| Stearidonic acid (C18:4) | 0.5 |
| Eicosenoic acid (C20:1) | 7.0 |
| Arachidonic acid (C20:4) | 1.2 |
| Eicosapentaenoic acid (C20:5) | 5.4 |
| Docosanoic acid (C22:0) | 3.7 |
| Docosapentaenoic acid (C22:5) | 1.7 |
| Docosahexaenoic acid (C22:6) | 3.5 |
| Tetracosanoic acid (C24:0) | 1.1 |

Example 1

1—Obtaining Formulations Made Up of Ratfish Liver Oil with Monoolein (Lipid Vehicle) and a Supercritical Rosemary Extract (Bioactive Compound) in Different Proportions.

The mixture of ratfish liver oil (RLO) (Phosphotech, France) with food-grade monoolein (MO) (Sigma-Aldrich Chemie GmbH, Steinheim, Germany) at a molar ratio of 1:1 was mixed with commercial supercritical rosemary extract (SRE) (ESTABILOTON OS) at different concentrations, including 4, 9 and 16% (w/w), to give rise to the formulations referred to hereinafter as RLO+MO+4% SRE, RLO+MO+9% SRE and RLO+MO+16% SRE. These mixtures were then made to go through a high-pressure homogenizer at 500 bar (Emulsiflex C5, Avestin Europe) three times.

2—Evaluating Gastrointestinal Digestion (GTI) In Vitro

For gastric digestion, 3 g of formulation (RLO+MO+4% SRE, RLO+MO+9% SRE and RLO+MO+16% SRE) were mixed with 600 MAG of phospholipids (PLs) (Phospholipon 90H) to simulate dietary PLs, and 16.4 mL of a gastric simulation solution (0.15 M NaCl at pH 2.5, SGF). The pH was adjusted to 2.5 with 1 M HCl. The prepared medium was pre-emulsified by means of homogenization at 3500 rpm for 2 minutes, temperature-controlled at 37° C. and stirred continuously at 200 rpm in an orbital stirrer (IKA KS 4000 is Control, Staufen, Germany). A 16% (w/v) solution containing pepsin of porcine origin (EC 3.4.23.1, Sigma-Aldrich Chemie GmbH, Steinheim, Germany) in SGF (pH 2.5) (activity 3300 U/MAG of protein) was then added in an enzyme:substrate proportion of 1:12 (w:w) and incubated at 37° C. for 1 hour.

For intestinal digestion, 6 mL of the gastric digest were mixed with 26 mL of 0.1 M trizma-maleate buffer, pH 7.5. The prepared medium was pre-emulsified by means of homogenization at 3500 rpm for 2 minutes.

On the other hand, a solution with a composition similar to bile secretion was prepared. To that end, 200 MAG of egg yolk phosphatidylcholine (Lipoid, Ludwigshafen, Germany), 500 MAG of bile salts, 40 MAG of cholesterol (Sigma-Aldrich Chemie GmbH, Steinheim, Germany), 1 mL of 325 mM $CaCl_2$, 3 mL of 3.25 M NaCl (Panreac Quimica S.A.U, Barcelona, Spain) and 20 mL of trizma-maleate buffer were mixed, and it was all homogenized at 3500 rpm for 2 minutes. The pre-emulsified sample and the simulated bile secretion were then mixed and homogenized together at 3500 rpm for 2 minutes and the entire was transferred to a beaker with its temperature regulated at 37° C. and with continuous stirring at 1000 rpm. The intestinal digestion began with the addition of fresh extract of pancreatin of porcine origin which was prepared in the following manner: 1.167 g of pancreatin dissolved in 7 mL of trizma-maleate buffer, subsequently stirred for 10 minutes and centrifuged at 1600×g at 5° C. for 15 minutes. Six mL of aqueous supernatant obtained were added to the reaction medium together with 10 MAG of phospholipase A2 (Nagase Enzymes). To enable studying the progression of digestion over time, as well as evaluating the digestion end point, 1.5 mL aliquots of the reaction medium were taken at 0, 5, 15, 10, 30 and 60 minutes.

2.1 Lipid Extraction

To extract total lipids from the different aliquots taken during digestion, three consecutive extractions were done with different solvent mixtures at a sample:solvent ratio=1:3 (v/v) and centrifuging for 10 minutes at 14500 rpm each time. The mixtures were, from the lowest to highest polarity:

i) n-hexane:methyl-tert-butyl-ether (MTBE) (50:50, v:v); ii) MTBE:petroleum ether (PE) (50:50, v:v); iii) PE:ethanol (1:0.6, v:v).

At the end of each extraction, the upper organic phase containing lipid components was collected, left to settle for 2 hours with anhydrous sodium sulfate (Sigma-Aldrich) to assure the removal of possible traces of water from the sample, and the solvent was evaporated under a nitrogen stream at 40° C. until obtaining a residue having a constant weight. The residues were then diluted in chloroform to a final concentration of 20 MAG/mL and analyzed using LC-ELSD.

The LC-ELSD analyses were performed using Agilent Technologies series 1200 liquid chromatograph (Santa Clara, Calif., USA) coupled to an ELSD (Agilent 1260 Infinity). The ELSD conditions were $2 \times 10^5$ Pa, 50° C., and a gain of 4 which was adjusted to accurately quantify minor compounds. Chromatographic separations were performed in an Agilent Poroshell 120 column (Sil 2.7 μm, 4.6×100 mm) at 35° C., a flow rate of 2 mL/min and by mixing three eluents (A, 100% isooctane; B, 0.02% (v/v) formic acid in isooctane:MTBE (50:50 v/v); and C, MTBE:propan-2-ol (50:50 v/v)) to form a ternary gradient that has been previously described by Torres et al. (2005). The injection volume was 1 μL.

3—Determining In Vitro Bioaccessibility 3.1 Phase Separation

In order to separate the undigested lipid fraction from the lipid products incorporated in micellar structures during the in vitro intestinal digestion process, the digestion end product was centrifuged at 4000 rpm at 37° C. for 40 minutes, according to the protocol carried out by Soler-Rivas et al. (2010). After centrifugation, the digestion medium separated into 3 clearly differentiated phases: an upper phase, referred to as an oily phase (OP), made up of the fraction of the lipid sample that has not been digested and part of the rosemary extract. In in vivo conditions, this phase would be secreted with feces or converted by colonic microbiota; an intermediate aqueous phase, referred to as a micellar phase (MP), where the digested lipid fraction can be found forming micellar structures and vesicles with the incorporated rosemary extract. This is the bioaccessible fraction, i.e., the fraction available for absorption by intestinal epithelial cells; and a very inconsequential insoluble lower phase, referred to as a precipitate phase (PP), consisting of residues of fatty acid soaps and salts released during pancreatic digestion (5).

Once the phases have been separated, lipid extraction, sample preparation and LC-ELSD analysis were carried out as explained in the preceding section.

3.2 Total Polyphenol Measurement

The total polyphenol content of the bioaccessible fraction of the SRE delivered in the RLO+MO system was determined by means of the Folin-Ciocalteu method (6). Briefly, 10 μl of sample were mixed with 150 μl of Folin-Ciocalteu's solution and it was left for 3 minutes at room temperature. Then, 50 μL of a sodium bicarbonate solution (3%) were added. Finally, after incubating in darkness at 37° C. for 2 hours, absorbance at 735 nm was measured using a spectrophotometer (Genesis 10 UV Scanning, Thermo Scientific). The rosemary extract itself and rosmarinic acid at different concentrations (0.2-2 MAG/mL) were used as standards.

4—In Vitro Antiproliferative Activity Study

The in vitro antiproliferative activity of the (bioaccessible) micellar phases obtained after the digestion of formulations RLO+MO+4% SRE, RLO+MO+9% SRE and RLO+MO+16% SRE was evaluated in human colon cancer cell models.

4.1 Cell Cultures

Human colon cancer cell line SW620 was cultured in DMEM medium supplemented with 10% of FBS, 2 mM of glutamine and 1% of antibiotic-antimycotic solution, containing 10000 units/mL of base penicillin, 10000 μg/mL of base streptomycin and 25000 ng/mL of amphotericin B. The cell culture was kept under standard temperature (37° C.), humidity (95%) and carbon dioxide (5%) conditions.

4.2 Cell Viability Assay

The MTT (3-(4,5-dimethylthiazol-2-yl)-2,5-diphenyltetrazolium bromide) method was used to measure the antiproliferative activity of the digestion products. To that end, cells in exponential growth phase were transferred to 24-well plates, where an average of 25000 cells per well were incorporated in a final volume of 200 μL. After incubating at 37° C. for 2 hours, the culture medium was replaced with medium containing the bioaccessible fraction (MP) of each of the assayed products (RLO+MO+4% SRE, RLO+MO+9% SRE and RLO+MO+16% SRE), diluted in DMEM culture medium at different concentrations (0-11.5 MP μL·mL$^{-1}$). Cell viability was determined both at the time of treatment, in order to control the starting cell population, and after incubating the plate at 37° C. for 48 hours, in order to determine the effect of the product on cell growth. To determine the number of viable cells, 20 μL of MTT solution (5 MAG/mL in FBS) were added to each well. The plate was then left to incubate for 3 hours for formazan (blue metabolite of MTT) to attach to the viable cells. After incubation, the medium was removed and 200 μL of DMSO (dimethyl sulfoxide) were added to disassociate the cells and re-suspend formazan, the concentration of which (measured at 560 nm with a spectrophotometric plate reader (UVM 340 Biochrom, CambriDAGe)) is directly related to the number of viable cells. The concentration values of each of the products corresponding to IC50 (50% of inhibited cell viability) were calculated according to NIH definitions using logistic regression, a concept described as the relationship between the response to treatment with medicinal products and the dose or concentration of said medicinal product.

Example 2

1—Obtaining Formulations Made Up of the Product Obtained from RLO by Means of a Pilot Plant-Scalable Enzymatic Glycerolysis Process (Lipid Vehicle) and a Supercritical Rosemary Extract (Bioactive Compound) in Different Proportions.

The glycerolysis product (GP) mixture obtained from ratfish liver oil (RLO) (Phosphotech, France) under the stirring, temperature and time conditions (continuous stirring at 200 rpm and 40° C. for 48 hours) illustrated in the materials and methods (see the optimized enzymatic glycolysis method) was mixed with commercial supercritical rosemary extract (SRE) (ESTABILOTON OS) at different concentrations, including 4, 9 and 16% (w/w), to give rise to the formulations referred to hereinafter as GP+4% SRE, GP+9% SRE and GP+16% SRE. These mixtures were then made to go through a high-pressure homogenizer at 500 bar (Emulsiflex C5, Avestin Europe) three times.

In the present invention, the term "optimum reaction conditions" refers to the glycerolysis conditions, including the type of biocatalyze and enzyme:substrate ratio, temperature, proportion of glycerin, reaction time and the absence/presence of solvents, leading to the formation of more than 25% (w/w) of monoacylglycerol and the complete disappearance of the triglyceride present in RLO.

2—Evaluating Gastrointestinal Digestion (GTI) In Vitro

For gastric digestion, 3 g of formulation (GP+4% SRE, GP+9% SRE and GP+16% SRE) were mixed with 600 MAG of phospholipids (PLs) (Phospholipon 90H) to simulate dietary PLs, and 16.4 mL of a gastric simulation solution (0.15 M NaCl at pH 2.5, SGF). The pH was adjusted to 2.5 with 1 M HCl. The prepared medium was pre-emulsified by means of homogenization at 3500 rpm for 2 minutes, temperature-controlled at 37° C. and stirred continuously at 200 rpm in an orbital stirrer (IKA KS 4000 is Control, Staufen, Germany). A 16% (w/v) solution containing pepsin of porcine origin (EC 3.4.23.1, Sigma-Aldrich Chemie GmbH, Steinheim, Germany) in SGF (activity 3300 U/MAG of protein) was then added in an enzyme:substrate proportion of 1:12 (w:w) and incubated at 37° C. for 1 hour.

For intestinal digestion, 6 mL of the gastric digest were mixed with 26 mL of 0.1 M trizma-maleate buffer, pH 7.5. The prepared medium was pre-emulsified by means of homogenization at 3500 rpm for 2 minutes.

On the other hand, a solution with a composition similar to bile secretion was prepared. To that end, 200 MAG of egg yolk phosphatidylcholine (Lipoid, Ludwigshafen, Germany), 500 MAG of bile salts, 40 MAG of cholesterol (Sigma-Aldrich Chemie GmbH, Steinheim, Germany), 1 mL of 325 mM $CaCl_2$, 3 mL of 3.25 M NaCl (Panreac Quimica S.A.U, Barcelona, Spain) and 20 mL of trizma-maleate buffer were mixed, and it was all homogenized at 3500 rpm for 2 minutes. The pre-emulsified sample and the simulated bile secretion were then mixed and homogenized together at 3500 rpm for 2 minutes and the entire was transferred to a beaker with its temperature regulated at 37° C. and with continuous stirring at 1000 rpm. The intestinal digestion began with the addition of fresh extract of pancreatin of porcine origin which was prepared in the following manner: 1.167 g of pancreatin dissolved in 7 mL of trizma-maleate buffer, subsequently stirred for 10 minutes and centrifuged at 1600×g at 5° C. for 15 minutes. Six mL of aqueous supernatant obtained were added to the reaction medium together with 10 MAG of phospholipase A2 (Nagase Enzymes). To enable studying the progression of digestion over time, as well as evaluating the digestion end point, 1.5 mL aliquots of the reaction medium were taken at 0, 5, 15, 10, 30 and 60 minutes.

2.1 Lipid Extraction

To extract total lipids from the different aliquots taken during digestion, three consecutive extractions were done with different solvent mixtures at a sample:solvent ratio=1:3 (v/v) and centrifuging for 10 minutes at 14500 rpm each time. The mixtures were, from the lowest to highest polarity: i) n-hexane:methyl-tert-butyl-ether (MTBE) (50:50, v:v); ii) MTBE:petroleum ether (PE) (50:50, v:v); iii) PE:ethanol (1:0.6, v:v).

At the end of each extraction, the upper organic phase containing lipid components was collected, left to settle for 2 hours with anhydrous sodium sulfate (Sigma-Aldrich) to assure the removal of possible traces of water from the sample, and the solvent was evaporated under a nitrogen stream at 40° C. until obtaining a residue having a constant weight. The residues were then diluted in chloroform to a final concentration of 20 MAG/mL and analyzed using LC-ELSD.

The LC-ELSD analyses were performed using Agilent Technologies series 1200 liquid chromatograph (Santa Clara, Calif., USA) coupled to an ELSD (Agilent 1260 Infinity). The ELSD conditions were $2 \times 10^5$ Pa, 50° C., and a gain of 4 which was adjusted to accurately quantify minor compounds. Chromatographic separations were performed in an Agilent Poroshell 120 column (Sil 2.7 μm, 4.6×100 mm) at 35° C., a flow rate of 2 mL/min and by mixing three eluents (A, 100% isooctane; B, 0.02% (v/v) formic acid in isooctane:MTBE (50:50 v/v); and C, MTBE:propan-2-ol (50:50 v/v)) to form a ternary gradient that has been previously described by Torres et al. (2005). The injection volume was 1 μL.

3—Determining In Vitro Bioaccessibility 3.1 Phase Separation

In order to separate the undigested lipid fraction from the lipid products incorporated in micellar structures during the in vitro intestinal digestion process, the digestion end product was centrifuged at 4000 rpm at 37° C. for 40 minutes, according to the protocol carried out by Soler-Rivas et al. (2010). After centrifugation, the digestion medium separated into 3 clearly differentiated phases: an upper phase, referred to as an oily phase (OP), made up of the fraction of the lipid sample that has not been digested and part of the rosemary extract. In vivo conditions, this phase would be secreted with feces or converted by colonic microbiota; an intermediate aqueous phase, referred to as a micellar phase (MP), where the digested lipid fraction can be found forming micellar structures and vesicles with the incorporated rosemary extract. This is the bioaccessible fraction, i.e., the fraction available for absorption by intestinal epithelial cells; and a very inconsequential insoluble lower phase, referred to as a precipitate phase (PP), consisting of residues of fatty acid soaps and salts released during pancreatic digestion (5).

Once the phases have been separated, lipid extraction, sample preparation and LC-ELSD analysis were carried out as explained in the preceding section.

3.2 Total Polyphenol Measurement

The total polyphenol content of the bioaccessible fraction of the SRE delivered in the GP system was determined by means of the Folin-Ciocalteu method (6). Briefly, 10 μl of sample were mixed with 150 μl of Folin-Ciocalteu's solution and it was left for 3 minutes at room temperature. Then, 50 μL of a sodium bicarbonate solution (3%) were added. Finally, after incubating in darkness at 37° C. for 2 hours, absorbance at 735 nm was measured using a spectrophotometer (Genesis 10 UV Scanning, Thermo Scientific). The rosemary extract itself and rosmarinic acid at different concentrations (0.2-2 MAG/mL) were used as standards.

4—In Vitro Antiproliferative Activity Study

The in vitro antiproliferative activity of the (bioaccessible) micellar phases obtained after the digestion of formulations GP+4% SRE, GP+9% SRE and GP+16% SRE was evaluated in human colon cancer cell models.

4.1 Cell Cultures

Human colon cancer cell line SW620 was cultured in DMEM medium supplemented with 10% of FBS, 2 mM of glutamine and 1% of antibiotic-antimycotic solution, containing 10000 units/mL of base penicillin, 10000 μg/mL of base streptomycin and 25000 ng/mL of amphotericin B. The cell culture was kept under standard temperature (37° C.), humidity (95%) and carbon dioxide (5%) conditions.

4.2 Cell Viability Assay

The MTT (3-(4,5-dimethylthiazol-2-yl)-2,5-diphenyltetrazolium bromide) method was used to measure the antiproliferative activity of the digestion products. To that end, cells in exponential growth phase were transferred to 24-well plates, where an average of 25000 cells per well were incorporated in a final volume of 200 μL. After incubating at 37° C. for 2 hours, the culture medium was replaced with medium containing the bioaccessible fraction (MP) of each of the assayed products (GP+4% SRE, GP+9% SRE and GP+16% SRE), diluted in DMEM culture medium at different concentrations (0-11.5 MP µL/mL). Cell viability was determined both at the time of treatment, in order to control the starting cell population, and after incubating the plate at 37° C. for 48 hours, in order to determine the effect of the product on cell growth. To determine the number of viable cells, 20 µL of MTT solution (5 MAG/mL in FBS) were added to each well. The plate was then left to incubate for 3 hours for formazan (blue metabolite of MTT) to attach to the viable cells. After incubation, the medium was removed and 200 µL of DMSO (dimethyl sulfoxide) were added to disassociate the cells and re-suspend formazan, the concentration of which (measured at 560 nm with a spectrophotometric plate reader (UVM 340 Biochrom, CambriDAGe)) is directly related to the number of viable cells. The concentration values*/*/ of each of the products corresponding to IC50 (50% of inhibited cell viability) were calculated according to NIH definitions using logistic regression, a concept described as the relationship between the response to treatment with medicinal products and the dose or concentration of said medicinal product.

Example 3

1—In Vitro Gastrointestinal Digestion of Non-Delivered Supercritical Rosemary Extract (Bioactive Compound) in Different Proportions For gastric digestion, 120, 270 and 480 MAG of commercial SRE (amount equivalent to that present in formulations with 4, 9 and 16% of delivered SRE, respectively) were mixed with 600 MAG of phospholipids (PLs) (Phospholipon 90H) to simulate dietary PLs, and 16.4 mL of a gastric simulation solution (0.15 M NaCl at pH 2.5, SGF). The pH was adjusted to 2.5 with 1 M HCl. The prepared medium was pre-emulsified by means of homogenization at 3500 rpm for 2 minutes, temperature-controlled at 37° C. and stirred continuously at 200 rpm in an orbital stirrer (IKA KS 4000 is Control, Staufen, Germany). A 16% (w/v) solution containing pepsin of porcine origin (EC 3.4.23.1, Sigma-Aldrich Chemie GmbH, Steinheim, Germany) in SGF (pH 2.5) (activity 3300 U/MAG of protein) was then added in an enzyme:substrate proportion of 1:12 (w:w) and incubated at 37° C. for 1 hour.

For intestinal digestion, 6 mL of the gastric digest were mixed with 26 mL of 0.1 M trizma-maleate buffer, pH 7.5. The prepared medium was pre-emulsified by means of homogenization at 3500 rpm for 2 minutes.

On the other hand, a solution with a composition similar to bile secretion was prepared. To that end, 200 MAG of egg yolk phosphatidylcholine (Lipoid, Ludwigshafen, Germany), 500 MAG of bile salts, 40 MAG of cholesterol (Sigma-Aldrich Chemie GmbH, Steinheim, Germany), 1 mL of 325 mM $CaCl_2$, 3 mL of 3.25 M NaCl (Panreac Quimica S.A.U, Barcelona, Spain) and 20 mL of trizma-maleate buffer were mixed, and homogenized all together at 3500 rpm for 2 minutes. The pre-emulsified sample and the simulated bile secretion were then mixed and homogenized together at 3500 rpm for 2 minutes and the entire was transferred to a beaker with its temperature regulated at 37° C. and with continuous stirring at 1000 rpm. The intestinal digestion began with the addition of fresh extract of pancreatin of porcine origin which was prepared in the following manner: 1.167 g of pancreatin dissolved in 7 mL of trizma-maleate buffer, subsequently stirred for 10 minutes and centrifuged at 1600×g at 5° C. for 15 minutes. Six mL of aqueous supernatant obtained were added to the reaction medium together with 10 MAG of phospholipase A2 (Nagase Enzymes) and it was incubated at 37° C. for 60 minutes.

2—Determining In Vitro Bioaccessibility 2.1 Phase Separation

In order to separate the bioaccessible fraction of the SRE from the non-bioaccessible fraction due to degradation or precipitation during the digestive process, the digestion end product was centrifuged at 4000 rpm at 37° C. for 40 minutes, according to the protocol carried out by Soler-Rivas et al. (2010).

2.2 Total Polyphenol Measurement

The total polyphenol content of the bioaccessible fraction of the non-delivered SRE was determined by means of the Folin-Ciocalteu method (6). Briefly, 10 µl of sample were mixed with 150 µl of Folin-Ciocalteu's solution and it was left for 3 minutes at room temperature. Then, 50 µL of a sodium bicarbonate solution (3%) were added. Finally, after incubating in darkness at 37° C. for 2 hours, absorbance at 735 nm was measured using a spectrophotometer (Genesis 10 UV Scanning, Thermo Scientific). The rosemary extract itself and rosmarinic acid at different concentrations (0.2-2 MAG/mL) were used as standards.

3—In Vitro Antiproliferative Activity Study

The in vitro antiproliferative activity of the (bioaccessible) micellar phases obtained after the digestion of the non-delivered SRE was evaluated in human colon cancer cell models.

3.1 Cell Cultures

Human colon cancer cell line SW620 was cultured in DMEM medium supplemented with 10% of FBS, 2 mM of glutamine and 1% of antibiotic-antimycotic solution, containing 10000 units/mL of base penicillin, 10000 µg/mL of base streptomycin and 25000 ng/mL of amphotericin B. The cell culture was kept under standard temperature (37° C.), humidity (95%) and carbon dioxide (5%) conditions.

3.2 Cell Viability Assay

The MTT (3-(4,5-dimethylthiazol-2-yl)-2,5-diphenyltetrazolium bromide) method was used to measure the antiproliferative activity of the digestion products. To that end, cells in exponential growth phase were transferred to 24-well plates, where an average of 25000 cells per well were incorporated in a final volume of 200 µL. After incubating at 37° C. for 2 hours, the culture medium was replaced with medium containing the bioaccessible fraction (MP) of each of the assayed products (4% of SRE, 9% of SRE and 16% non-delivered SRE), diluted in DMEM culture medium at different concentrations (0-11.5 MP µL/mL). Cell viability was determined both at the time of treatment, in order to control the starting cell population, and after incubating the plate at 37° C. for 48 hours, in order to determine the effect of the product on cell growth. To determine the number of viable cells, 20 µL of MTT solution (5 MAG/mL in FBS) were added to each well. The plate was then left to incubate for 3 hours for formazan (blue metabolite of MTT) to attach to the viable cells. After incubation, the medium was removed and 200 µL of DMSO (dimethyl sulfoxide) were added to disassociate the cells and re-suspend formazan, the concentration of which (measured at 560 nm with a spectrophotometric plate reader (UVM 340 Biochrom, CambriDAGe)) is directly related to the number of viable cells. The concentration values of each of the products corresponding to IC50 (50% of inhibited cell viability) were calculated according to NIH definitions using logistic regression, a concept described as the relationship between the response to treatment with medicinal products and the dose or concentration of said medicinal product.

Example 4

1—In Vitro Antiproliferative Activity Study of the Non-Digested and Non-Delivered Supercritical Rosemary Extract The in vitro antiproliferative activity of the non-digested and non-delivered SRE was evaluated in human colon cancer cell models.

1.1 Cell Cultures

Human colon cancer cell line SW620 was cultured in DMEM medium supplemented with 10% of FBS, 2 mM of glutamine and 1% of an antibiotic-antimycotic solution, containing 10000 units/mL of base penicillin, 10000 μg/mL of base streptomycin and 25000 ng/mL of amphotericin B. The cell culture was kept under standard temperature (37° C.), humidity (95%) and carbon dioxide (5%) conditions.

1.2 Cell Viability Assay

The MTT (3-(4,5-dimethylthiazol-2-yl)-2,5-diphenyltetrazolium bromide) method was used to measure the antiproliferative activity of the digestion products. To that end, cells in exponential growth phase were transferred to 24-well plates, where an average of 25000 cells per well were incorporated in a final volume of 200 μL. After incubating at 37° C. for 2 hours, the culture medium was replaced with medium containing the SRE at different concentrations (0-100 μg/mL). Cell viability was determined both at the time of treatment, in order to control the starting cell population, and after incubating the plate at 37° C. for 48 hours, in order to determine the effect of the product on cell growth. To determine the number of viable cells, 20 μL of MTT solution (5 MAG/mL in FBS) were added to each well. The plate was then left to incubate for 3 hours for formazan (blue metabolite of MTT) to attach to the viable cells. After incubation, the medium was removed and 200 μL of DMSO (dimethyl sulfoxide) were added to disassociate the cells and re-suspend formazan, the concentration of which (measured at 560 nm with a spectrophotometric plate reader (UVM 340 Biochrom, CambriDAGe)) is directly related to the number of viable cells. The concentration values of each of the products corresponding to IC50 (50% of inhibited cell viability) were calculated according to NIH definitions using logistic regression, a concept described as the relationship between the response to treatment with medicinal products and the dose or concentration of said medicinal product.

Example 5

1. Evaluating Gastrointestinal Digestion (GTI) In Vitro

The in vitro digestion GTI model used consists of two consecutive phases, a gastric phase (pH 2.5, 37° C., 1 hour in the presence of pepsin) and an intestinal phase (pH 7.4, 37° C., 1 hour in the presence of pancreatin). In the present invention, the gastric phase was used not so much for digesting the carrier lipid, but for studying the effect of the acidic pH and aqueous medium in the stomach on the stability of the delivered ingredient or drug. In terms of the intestinal phase, in order to reproduce the physiological results observed in the literature in terms of the degree of hydrolysis and the level of generated lipid species [Hofmann and Borgstrom, 1964], the conditions used during this step (enzyme/substrate ratio, lecithin/bile salts ratio, digestion time, pH and mineral composition of the digestive fluids) simulate the physiological conditions during intestinal digestion of lipids.

The behavior of each of the lipid systems during the digestion process depends on its initial lipid composition and will largely determine its behavior as a lipid vehicle as well as its bioaccessibility, and therefore bioactivity.

The digestibility of each of the lipid systems and formulations with SRE (see Examples 1 to 4) of the invention was evaluated by means of determining the hydrolysis of DAGE and TAG and the formation of the hydrolysis products (free fatty acid (FFA), DAG, MAGE and MAG) during the digestion process. To that end, lipid extraction of each of the aliquots collected during digestion was first carried out, and the exhaustive characterization of their composition was then carried out using LC-ELSD.

Due to the absence of lipase in the digestion medium, the lipid profile did not change with respect to the initial lipid profile during the gastric phase. However, during the intestinal phase, lipids are essentially hydrolyzed by pancreatic lipase, such that the digests have a lipid composition different from the initial lipid composition.

Figure 2:
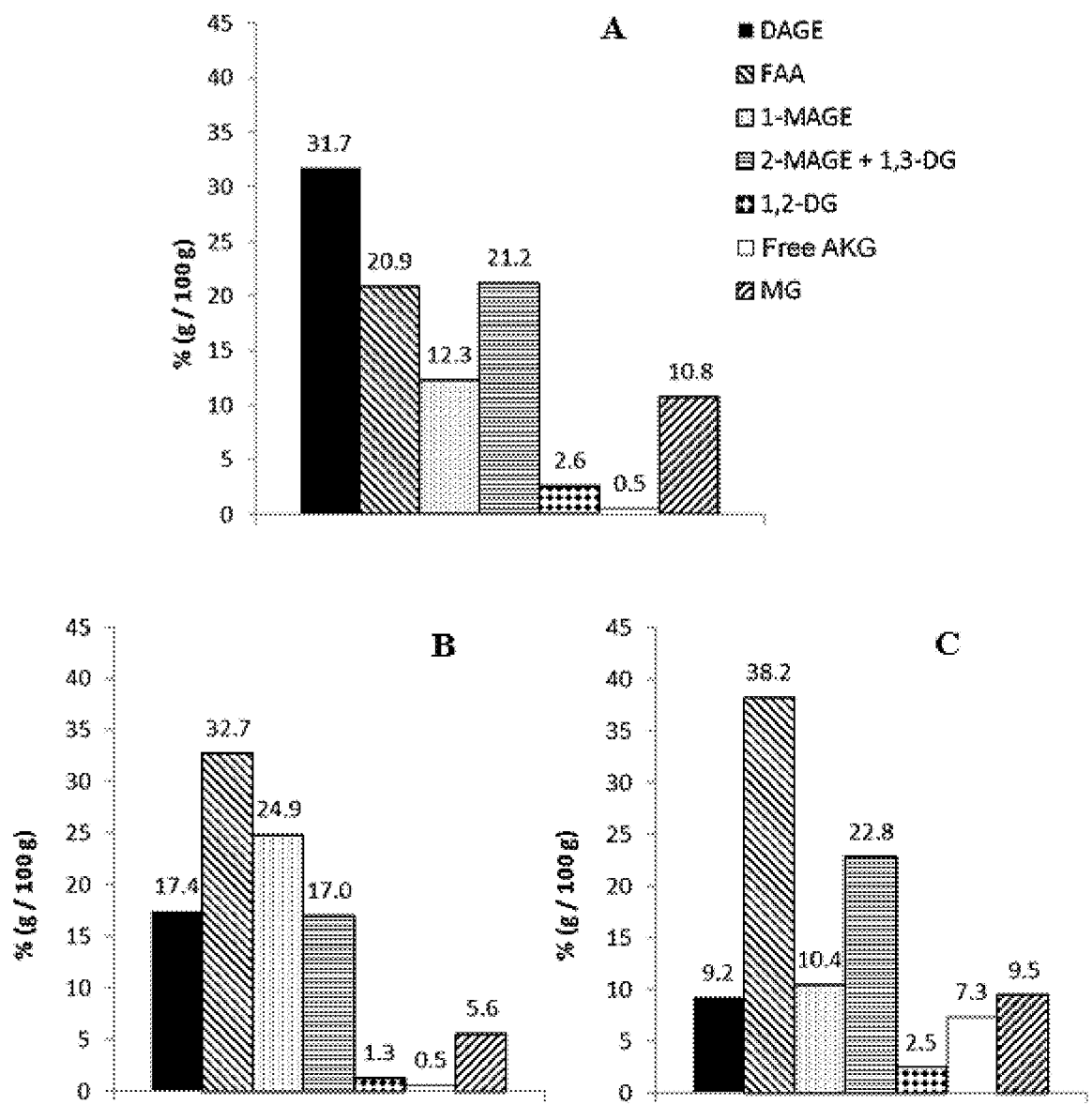
FIG. 2 shows the composition of the lipid mixture of the end products of the digestion of original RLO (A), RLO+MO (B), and GP (C) determined using LC-ELSD.

FIG. 2 shows the composition of the lipid mixture of the end products of the digestion of original RLO (FIG. 2A), RLO+MO (FIG. 2B) and GP (FIG. 2C). In all cases, TAGs were completely hydrolyzed, whereas at the end of the digestion process, non-hydrolyzed DAGEs were still detected. Therefore, as observed in FIG. 2, the highest degree of DAGE hydrolysis and FFA, DAG, MAGE and MAG formation was observed for the GP, followed by the RLO+MO system. Original RLO, with the highest initial DAGE content, was the least digestible of all the studied systems. These results furthermore indicate that the presence of an emulsifier in the medium favors digestion. Lipids with an emulsifying character, such as MAG, therefore improve lipid dispersion at the start of digestion in comparison with TAGs and DAGEs, which can favor an improved hydrolysis and a greater formation of micellar structures, where the digestion products can be more readily included. The highest percentage of free (non-esterified) AKG of the end product of the digestion of the GP with respect to the percentage of digests of the RLO+MO system and original RLO must also be highlighted. This can be attributed to the higher initial MAGE content of the GP, which is preferably hydrolyzed before DAGE to yield free AKG.

In terms of the digestion of formulations with rosemary, the presence of 4% (w/w) and 9% (w/w) of SRE did not change the digestion of the lipid vehicle (GP and RLO+MO), since no significant differences were observed with respect to rosemary-free systems. However, in the formulations with 16% of SRE, the digestibility of the lipid fraction is significantly lower (smaller degree of DAGE hydrolysis and less FFA, MAGE, DAG and MAG formation). This is due to the inhibition of pancreatic lipase in the presence of a high proportion of rosemary extract.

2. Determining In Vitro Bioaccessibility

Before the bioaccessibility study, the end products of the digestion were centrifuged at 4000 rpm and 37° C. for 40 minutes. After centrifugation, the digestion medium separated into 3 clearly differentiated phases: an upper phase, referred to as an oily phase (OP), made up of the fraction of the lipid sample that has not been digested and part of the rosemary extract. In in vivo conditions, this phase would be secreted with feces or converted by colonic microbiota; a very inconsequential insoluble lower phase, referred to as a precipitate phase (PP), consisting of residues of fatty acid soaps and salts released during pancreatic digestion; and an intermediate aqueous phase, referred to as a micellar phase (MP), where the lipid fraction digested by pancreatic lipase and emulsified with bile salts and phospholipids secreted by the gallbladder can be found forming micellar structures and vesicles (together with the incorporated SRE, in the case of formulations with extract). This is the bioaccessible fraction, i.e., the fraction available for absorption by intestinal epithelial cells.

Figure 3:
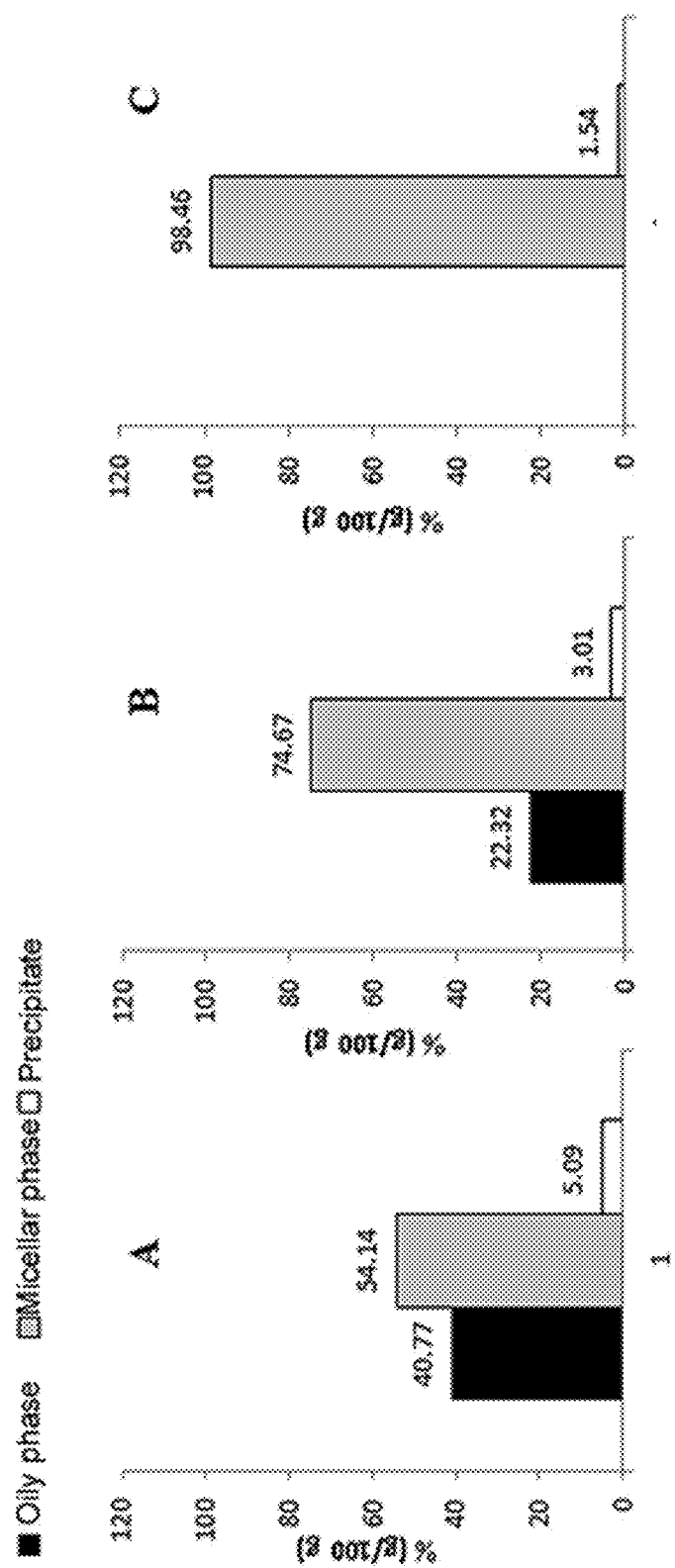
FIG. 3 shows the distribution of all the lipid products present in the end products of the digestion of original RLO (A), RLO+MO (B) and GP (C) between the oily phase (OP), micellar phase (MP) and precipitate phase (PP).

The bioaccessibility of the lipid systems of the invention (RLO, RLO+MO and GP), formulations with incorporated SRE (RLO+MO+SRE and GP+SRE) and non-delivered SRE was evaluated using LC-ELSD by means of characterizing the bioaccessible or micellar phase fraction of each of them. As shown in FIG. 3, the bioaccessible or micellar phase (MP), made up essentially of the digestion products (FFA, MAGE, DAG and MAG), is generally the main phase for all the studied digests. However, according to the results derived from the digestibility study, micellar phase is particularly abundant in the end product of the digestion of the GP, in which about 98.5% (w/w) of the lipid fraction is in the form of mixed micelles or vesicles, indicating that virtually all the products released from GP hydrolysis are potentially bioaccessible. The RLO+MO system, and particularly original RLO, are significantly less bioaccessible than the GP, since only about 75 and 54% (w/w), respectively, of the lipid fraction is in the MP, whereas about 22 and 41% (w/w), respectively, is part of the oily phase, made up essentially of undigested DAGE and MAGE. It must be pointed out that in the digested GP, MAGE is mainly in micellar form and is therefore bioaccessible. Likewise, it is also important to highlight the high percentage of free AKG (about 7.5% w/w) in the MP of the digested GP in comparison with that in the MP of the RLO+MO system (about 1% w/w) and original RLO (about 0.7% w/w) (FIG. 4). According to various studies carried out previously with colon cancer cell cultures, both MAGE, and particularly free AKG, are potentially more bioactive than DAGE.

Based on the digestibility and bioaccessibility results, original RLO was ruled out as a potentially effective vehicle for the SRE. This is why SRE formulations are only obtained in the present invention with GP (GP+SRE) and RLO+MO (RLO+MO+SRE) lipid systems. The incorporation of 4% (w/w) and 9% (w/w) of SRE does not significantly affect the bioaccessibility of the lipid fraction, observing a distribution of phases (OP, MP and PP) and a lipid composition of each of said phases similar to that of the SRE-free GP and RLO+MO systems (FIG. 4). However, in formulations with 16% of SRE, the lipid fraction is clearly less bioaccessible than in SRE-free systems, a higher percentage of lipid compounds in oily phase and a significant reduction of the MP being observed. These results are in accordance with the reduction of lipid digestibility observed previously in these formulations as a result of the high percentage of SRE.

The bioaccessibility of the SRE in the GP+SRE and RLO+MO+SRE formulations, and of the non-delivered SRE, was evaluated by means of determining the total polyphenols in the MP according to the Folin-Ciocalteu method. The non-delivered SRE has a relatively low bioaccessibility at the intestinal level, since only about 39% MP is detected with respect to the initial content before digestion. As discussed above, this can be attributed to the degradation or precipitation of the extract during the gastric digestion phase. With both lipid vehicles (GP and RLO+MO), however, the bioaccessibility of the SRE improves significantly with respect to the of the extract that is not delivered, particularly with the GP, since the GP+SRE formulations show about 91% of SRE in the MP with respect to the initial content (compared to 84% observed in the MP when RLO+MO is the lipid vehicle).

3. In Vitro Antiproliferative Activity Study

The antiproliferative activity of the lipid systems of the invention (RLO, RLO+MO and GP), formulations with the incorporated SRE (RLO+MO+SRE and GP+SRE) and (digested and non-digested) non-delivered SRE was evaluated in human colon cancer cell cultures (line SW620) by means of the MTT (3-(4,5-dimethylthiazol-2-yl)-2,5-diphenyltetrazolium bromide) method. To that end, the cells were treated with the bioaccessible fractions (MP) of the lipid systems, formulations with SRE and non-delivered SRE, diluted in DMEM culture medium at different concentrations (0-11.5 μL MP/mL). In the case of the non-digested and non-delivered SRE, the cells were treated with different concentrations of the extract in DMSO (0-100 μg/mL). Cell viability was determined at the time of treatment, in order to control the starting cell population, and after incubating at 37° C. for 48 hours, in order to determine the effect of the product on cell growth. The parameter used to estimate the antiproliferative activity of the products was the IC50 (50% of inhibited cell viability), which is described as the relationship between the response to treatment with medicinal products and the dose or concentration of said medicinal product. To enable validating the results, three independent experiments were carried out at least in triplicate (n=9).

Table 3 shows the IC50 values (MP concentration (μL/mL) inhibiting cell viability by 50%) of all the assayed products.

TABLE 3

|  |  | IC50 (μL MP/mL) |
|---|---|---|
| Lipid vehicles | Original RLO | 5.07 ± 0.09 |
|  | RLO + MO | 4.75 ± 0.26 |
|  | GP | 2.10 ± 0.02 |
| Formulations with SRE | RLO + MO + 4% SRE | 4.73 ± 0.07 |
|  | RLO + MO + 9% SRE | 4.21 ± 0.29 |
|  | GP + 4% SRE | 2.15 ± 0.12 |
|  | GP + 9% SRE | 0.92 ± 0.10 |
|  | GP + 16% SRE | 2.03 ± 0.08 |
| Non-delivered SRE | 9% SRE, digested | n.a* |
|  | SRE, non-digested | 42.33 ± 0.22** |

*n.a = IC50 not reached.
**IC50 = μg/mL of non-digested and non-delivered SRE inhibiting cell viability by 50%.

The GP showed an IC50 that is significantly lower than that of original RLO and the RLO+MO system. Such results indicate a greater antiproliferative effect of the bioaccessible fraction of the GP, which is directly related to the greater bioaccessibility observed for the GP, and accordingly, to the higher percentage of total bioactive alkylglycerols (AKG$_t$), and essentially of free AKG, in micellar or bioaccessible form (FIG. 4). It is also important to point out that in the case of the RLO+MO system, the addition of MO to RLO entails dilution of the total alkylglycerol content, which may be related to the lower antiproliferative effect observed.

The viability of cells treated with formulations with 4% SRE (GP+4% SRE and RLO+MO+4% SRE) is similar to that of the lipid systems separately, no significant differences being observed in the IC50 values (Table 1).

However, the results observed for formulations with 9% of SRE (GP+9% SRE and RLO+MO+9% SRE), which show an IC50 value less than that of the lipid systems separately, are of particular interest, this being particularly significant in the case of the GP+9% SRE formulation (Table 1). The bioaccessible fraction of the non-delivered SRE (with an initial amount of SRE similar to that of formulations with 9% of delivered SRE) had no effect on cell viability (IC50 is not reached for any of the MP concentrations applied) as a result of its reduced bioaccessibility at the intestinal level (only 39% of the initial content). Based on this, the results obtained indicate that the delivery of 9% of SRE with the RLO+MO system, and particularly the GP system, efficiently increases SRE stability during digestion, and accordingly its bioaccessibility at the intestinal level and its antiproliferative effect.

Furthermore, in the case of the GP+9% SRE formulation, the bioactive ingredient (AKG and SRE) content of the MP at the concentration required to reach IC50 (50.23 µM AKG$_t$ and 3.14 µg/mL SRE) is less than for the GP (124.54 µM AKG$_t$) and the non-digested and non-delivered SRE (IC50~40 µg/mL) separately, indicating a synergistic effect between the lipid vehicle and the delivered SRE.

Finally, the incorporation of 16% of SRE to the GP does not give rise to an increased antiproliferative effect because the digestibility and bioaccessibility of the lipid fraction in this formulation are compromised as a result of the high proportion of SRE, a lower bioactive alkylglycerol content in the MP being observed.

Example 6. In Vitro Antiproliferative Activity Study on Human Pancreatic Cancer Cells The antiproliferative activity of the lipid systems (RLO, RLO+MO and GP), formulations with incorporated SRE (RLO+MO+9% SRE and GP+9% SRE) and (digested and non-digested) non-delivered SRE was evaluated in human pancreatic cancer cell cultures (line MiaPaca-2) by means of the MTT method.

Three independent experiments were performed with different cell strains and on different days. The trend observed in terms of the effect of treatments on cell viability was similar in the 3 experiments.

Among the studied lipid systems, the GP showed a greater effect on cell viability at lower concentrations in comparison with original RLO and RLO+MO. In terms of formulations with SRE, while the effect of RLO+MO+9% SRE on cell viability was similar to that observed with the rosemary-free RLO+MO system, the GP+9% SRE formulation inhibited cell viability more effectively that the SRE-free GP did. The viability of cells treated with 1% cyclopentanone did not change so it can be assumed that the inhibition of cell viability by the GP and GP+9% SRE was due to the bioactive ingredients of the treatments.

The parameter used to assess the effect of a compound on cell viability is the mean inhibitory concentration (IC50), which is the product concentration inhibiting cell viability by 50%, such that the lower the IC50 of a compound is, the greater its effect will be. The two treatments with a lower IC50 value, and are therefore more effective, were GP and GP+9% SRE. Original RLO and RLO+MO with and without SRE showed significantly higher IC50 values and the non-delivered SRE had no effect whatsoever on cell viability (did not inhibit viability by 50% at any of the studied concentrations).

The greater antiproliferative effect of the GP with respect to the other two studied lipid systems is probably due to its greater digestibility and bioaccessibility, and accordingly to the higher percentage of total bioactive AKGs (AKGt), and essentially of free AKG, in micellar or bioaccessible form. It is important to point out that in the case of the RLO+MO system, the addition of MO to RLO entails dilution of the total alkylglycerol content, which may be related to the lower antiproliferative effect observed in comparison with the effect of the GP.

With respect to the GP+9% SRE formulation, such a low IC50 value observed suggests a synergistic effect between the active ingredients of both ingredients.

The bioaccessible fraction of the digested, non-delivered SRE (with an initial amount of SRE similar to that of GP formulations with 9% of SRE) had no effect on cell viability (IC50 is not reached for any of the MP concentrations applied). This is due to the reduced bioaccessibility of non-delivered rosemary at the intestinal level (only 39% of the initial content). Based on this, the results obtained indicate that the delivery of 9% of SRE with the GP efficiently increases SRE stability during digestion, and accordingly its bioaccessibility at the intestinal level and its antiproliferative effect.

Table 4 shows the IC50 values (MP concentration (µL/mL) inhibiting cell viability by 50%) of all the assayed products.

TABLE 4

| | | IC$_{50}$ (µL MP/mL) |
|---|---|---|
| Lipid vehicles | Original RLO | 9.20 ± 0.04 |
| | RLO + MO | 7.60 ± 0.09 |
| | GP | 5.50 ± 0.76 |
| Formulations with SRE | RLO + MO + 9% SRE | 5.18 ± 0.68 |
| | PG + 9% SRE | 3.75 ± 0.19 |
| Non-delivered SRE | 9% of SRE, digested | n.a * |
| | SRE, non-digested | 48.69 ± 0.88** |

*n.a = IC$_{50}$ not reached.
**IC$_{50}$ = µg/mL of non-digested and non-delivered SRE inhibiting cell viability by 50%.

Example 7.—Immunomodulator Complement (Innate Response Potentiator)

7.1. Methodology

An 8-week double-blind, parallel, randomized study was conducted in which 57 healthy volunteers (58.6% being women) with a mean age of 27.9±10.1 years old were included, 30 of whom belonged to the study group and 27 to the control group.

The participants took one capsule with lunch or dinner. The soft gelatin capsules contained alkylglycerols, rosemary extract and monostearin of the following characteristics:

RLO: shark liver oil 20% alkylglycerols (Gustav Heess): 750 mg (providing 150 mg of alkylglycerols)

SRE: rosemary antioxidant extract, 25% diterpene phenols, type no. 027.020 (*Rosmarinus officinalis* L.) 45 mg (providing 11.25 mg of diterpene phenols)

MS: food-grade glycerol monostearate.

Composition: 91.2% RLO+5.2% SRE+3.6% MS

After drawing blood, PBMCs were isolated and then cultured with LPS for measuring cytokines in the supernatant, in which the levels of IL1β; IL 2, 4, 5, 6, 8, 10, IFNý, TNFα were measured using to that end Human High Sensitivity T Cell Magnetic Bead Panel kit and taking readings with MagPix.

The CD (cluster of differentiation) count was also performed for clusters of differentiation CD3+, CD4+; CD8+, CD14+, CD16+, CD56+ on CD45+, using to that end kits and antibodies that are specific for flow cytometry.

In addition to the anthropometric control, the control of vital signs and the recording of tolerance and adverse effects, the levels of urea, creatinine, liver enzymes GOT/GPT/

GGT, bilirubin and FA were evaluated as safety and follow-up parameters in the first, interim and final visits.

The immunomodulatory influence of the treatment was evaluated by generating an array of bivariate correlations (principal component analysis) for the purpose of showing the biological correlation between plasma concentrations of cytokines produced by mononuclear cells isolated from peripheral blood, and the immunological response (Th1, effector response, and Th2, tolerance response).

7.2. Results

Figure 5:
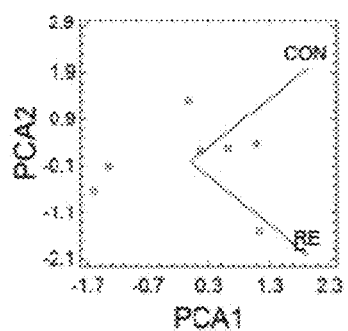
FIG. 5 shows the principal component analysis (PCA) considering the relative variations of the mean values in immune function biomarkers. Both components show contribution differences with Eigenvalues: PCA1, 1.21 and PCA2, 0.79, where the most relevant parameters in the segregation of the differential response between treated group and control are: IL4 (which decreases with SRE-RLO intervention), IL10 and IFNg (which increase with SRE-RLO intervention).

As shown in FIG. 5 which illustrates the cytokine profile of mononuclear cells stimulated in vitro, the principal component analysis indicates a trends towards a decrease of IL4, and a moderate increase of IL10 and IFNg associated with the nutritional supplement described in detail in the methodology which shows, on one hand, a suitable response of innate immune response activation and tolerance with intermediate polarization of M1/M2 macrophages and a cytokine profile that favors the maturation of effector cells (monocytes with phagocytic activity, NK cells with cytotoxic activity).

Additionally, phenotyping (CD differentiation markers) of the leukocyte population shows an increase (24%) in the leukocyte population (CD45$^+$) possibly derived from the use of rosemary extract SRE, an event which is not observed in other studies with the independent administration of RLO (Palmieri B, Pennelli A, Di Cerbo A. Jurassic surgery and immunity enhancement by alkylglycerols of shark liver oil. Lipids in Health and Disease 2014, 13:178). This increase is associated with significant changes in the markers of mature effector populations: monocytes (with functional differentiation towards a greater phagocytic activity) and NK cells (with potential cytotoxic activity against tumor cells).

Figure 6:
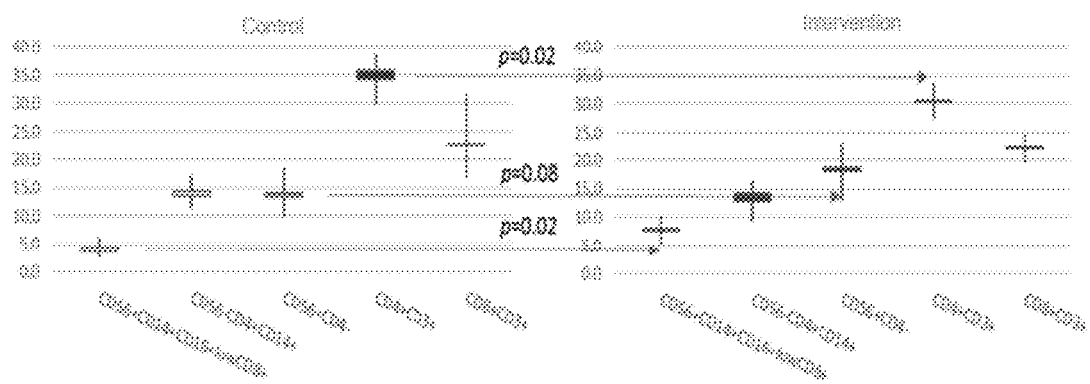
FIG. 6 shows the comparative analysis of leukocyte populations in healthy individuals after the intervention period with SRE (n=7). Statistically significant differences were calculated for CD56+CD4− and CD4+CD3+ populations. The resulting trend in the analyzed variables shows innate immune system polarization towards anti-inflammatory conditions that are favorable for a suitable potential development and maturation of effector cells (monocytes and NK cells) and the absence of T CD4+CD3+ (Th) expansion which, together with the observed cytokine profile, suggests a greater functional maturation.

On the other hand, the combination of the increase in IL-10 and the decrease in IL-4 suggests the absence of the expansion of regulatory T-cells and a more mature functional state of said T-cells (and therefore deviating from the immature state associated with pro-tumor processes) (FIG. 6).

In summary, the resulting trend in the cytokine profile and leukocyte phenotyping reflects an anti-inflammatory environment that is favorable towards the innate immune system polarization to effector cells of the following type: non-classical monocytes and NK cells with phagocytic capacity and cytotoxic activity preventing tumor development. Therefore, the analysis of immunological parameters (cytokines and leukocyte phenotyping) in volunteers who took the nutritional supplement for 8 weeks indicates a positive immunonutritional influence consisting of:

innate immune response activation and tolerance.
intermediate polarization of the immune response towards effector cells with phagocytic activity (monocytes) and cytotoxic activity (NK cells).
production of a cytokine profile with an anti-inflammatory and antitumor activity.

These results are surprising given that other studies that have been conducted with alkylglycerols alone have only shown the stimulation and activation of the adaptive response. However, in the present study where the alkylglycerols are complemented with SRE, a clear stimulation of the innate response along with an intermediate M1/M2 polarization, a unique effect found in this complement, is observed, where this modulation of the innate response is potentially effective both in cancer and in disorders of the immune system.

These results therefore suggest the use of this complement as:

Agent preventing the development of metastasis in patients with cancer with localized tumors.
Agent enhancing immunotherapy in candidate patients, in which activation of the innate response towards the production of mature effector cells with phagocytic capacity-monocytes, NK cells-, the production of cytokines with antitumor activity and the functional maturation of T-lymphocytes targeting tumor antigens, is required.
Agent preventing immunological disorders.

On the other hand, a significant decrease of the JAK1 gene was observed in the blood cells of volunteers who took the complement as indicated in the methodology for 8 weeks (see FIG. 7).

JAK1 is a kinase tyrosine protein that is essential in the signaling of certain type I and type II cytokines and in the signal transduction of interferons IFN-α/β/γ and members of the IL10-R family. The decrease thereof after the nutritional intervention may therefore attenuate the general inflammatory response (which is potentially useful in the event of low-grade inflammation).

On the other hand, the overexpression of the JAK1 gene in cancer has been associated with the promotion of metastasis. In the context of cancer, the present invention may furthermore contribute to stopping tumor and metastasis progression, not only as a result of its immunomodulating and anti-inflammatory activity, but also as a result of its specific effect on JAK1 pathway inhibition.

The expression of the NFE2L2 gene also decreased significantly in the treatment group. Nrf2 is a transcription factor associated with the expression of antioxidant proteins which reduce oxidative stress in the event of injury and inflammation.

Furthermore, it was observed that the expression of the BMP2 gene also decreased significantly in the treatment group. BMP2 belongs to the TNF superfamily and contributes to the initiation and development of colon cancer as it promotes CSC development, reflected in the increase of pluripotent cell markers (CD133+ and EpCAM+) along with the increase of drug resistance. An intervention capable of reducing the circulating levels of BMP2 may therefore contribute to reducing the number of colon cancer promoting stem cells.

Figure 8:
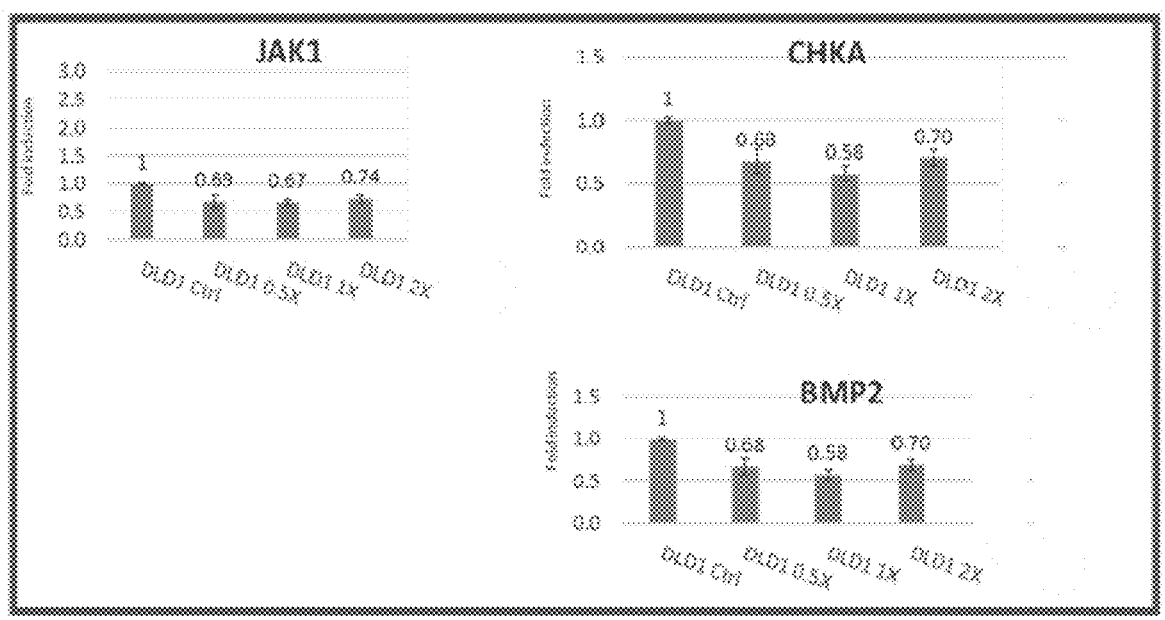
FIG. 8 shows the in vitro validation of genes regulated by the intervention in the clinical study in colon cancer tumor line DLD1.

The in vitro studies performed with rosemary extract and RLO and MS in human colon cancer tumor cells (SW620) validate the specific effect of SRE in reducing the expression of genes JAK1, CHOKA and BMP2 (FIG. 8)

Finally, the inhibition of CHKA was observed in the blood cells of volunteers who took the complement for 8 weeks, i.e., the extract described in the methodology, CHKA being the first enzyme of the Kennedy pathway for phosphatidylcholine biosynthesis, which is not only involved in the tumor process, but also in metabolic homeostasis, alterations of which were associated with different metabolic diseases associated with cancer, such as obesity or metabolic syndrome (FIG. 7).

The invention claimed is:

1. A composition comprising:
   a. about 5.2% (w/w) of a supercritical rosemary extract (SRE);
   b. about 91.2% (w/w) a lipid system comprising ratfish liver oil (RLO) or a product of an enzymatic or chemical glycerolysis processing of ratfish liver oil (RLO); and
   c. about 3.6% (w/w) of monostearin (MS).

2. A composition comprising: a supercritical rosemary extract (SRE) and a lipid system comprising a product of an enzymatic or chemical glycerolysis processing of ratfish liver oil (RLO), wherein the lipid system comprises:
   a. between 25% and 35% (w/w) of monoglycerides and/or free alkylglycerols;
   b. between 10% and 25% (w/w) of diacylglycerol ethers (DAGEs); and
   c. between 40% and 60% (w/w) of monoacylglycerol ethers (MAGEs) and/or diacylglycerols (DAGs), where the proportion of MAGEs with respect to the total amount of MAGEs and DAGs present in the lipid system is at least 50% (w/w).

3. A composition comprising: a supercritical rosemary extract (SRE) and a lipid system comprising a product of an enzymatic or chemical glycerolysis processing of ratfish liver oil (RLO), wherein the lipid system comprises:
   a. between 25% and 35% (w/w) of monoglycerides and/or free alkylglycerols;
   b. between 10% and 25% (w/w) of diacylglycerol ethers (DAGEs);
   c. between 0% and 5% (w/w) of triglycerides;
   d. between 0% and 3% of glycerin; and
   e. between 40% and 60% (w/w) of monoacylglycerol ethers (MAGEs) and/or diacylglycerols (DAGs), where the proportion of MAGEs with respect to the total amount of MAGEs and DAGs present in the lipid system is at least 50% (w/w).

4. A composition comprising: a supercritical rosemary extract (SRE) and a lipid system comprising a product of an enzymatic or chemical glycerolysis processing of ratfish liver oil (RLO), wherein the lipid system comprises:
   a. between 28% and 32% (w/w) of monoglycerides and/or free alkylglycerols;
   b. between 18% and 22% (w/w) of diacylglycerol ethers (DAGEs);
   c. between 0% and 2% (w/w) of triglycerides;
   d. between 1% and 3% of glycerin; and
   e. between 40% and 50% (w/w) of monoacylglycerol ethers (MAGEs) and/or diacylglycerols (DAGs), where the proportion of MAGEs with respect to the total amount of MAGEs and DAGs present in the lipid system is at least 50% (w/w).

5. The composition according to claim 1, wherein the composition is formulated as a pharmaceutically acceptable or food-grade vehicle for functional foods, nutraceutical products, natural extracts or drugs.

6. A food composition comprising the composition according to claim 1.

7. A pharmaceutical composition comprising the composition according to claim 1 and a pharmaceutically acceptable excipient.

8. The composition according to claim 5, wherein the drugs comprise anticancer drugs.

* * * * *